US009574239B2

(12) United States Patent
Croce

(10) Patent No.: US 9,574,239 B2
(45) Date of Patent: Feb. 21, 2017

(54) MICRORNA SIGNATURES IN HUMAN OVARIAN CANCER

(71) Applicant: The Ohio State University Research Foundation, Columbus, OH (US)

(72) Inventor: Carlo M. Croce, Columbus, OH (US)

(73) Assignee: The Ohio State University Research Foundation, Columbus, OH (US)

(*) Notice: Subject to any disclaimer, the term of this patent is extended or adjusted under 35 U.S.C. 154(b) by 0 days.

(21) Appl. No.: 14/485,995

(22) Filed: Sep. 15, 2014

(65) Prior Publication Data

US 2015/0024963 A1 Jan. 22, 2015

Related U.S. Application Data

(63) Continuation of application No. 12/676,670, filed as application No. PCT/US2008/075565 on Sep. 8, 2008, now abandoned.

(60) Provisional application No. 60/967,663, filed on Sep. 6, 2007.

(51) Int. Cl.

*G01N 33/574* (2006.01)
*C12Q 1/68* (2006.01)
*A61K 31/7088* (2006.01)

(52) U.S. Cl.

CPC ......... *C12Q 1/6886* (2013.01); *A61K 31/7088* (2013.01); *C12Q 2600/106* (2013.01); *C12Q 2600/112* (2013.01); *C12Q 2600/136* (2013.01); *C12Q 2600/154* (2013.01); *C12Q 2600/16* (2013.01); *C12Q 2600/178* (2013.01)

(58) Field of Classification Search

None
See application file for complete search history.

(56) References Cited

U.S. PATENT DOCUMENTS 7,955,848 B2 * 6/2011 Dmitrovsky .......... C12N 15/111 435/325

OTHER PUBLICATIONS

Zhang, et al. (2006, PNAS, v.103: 9136-9141).*
He, et al. (2005, PNAS, v.102, No. 52:19075-80).*
Van Rooij. (2011) "The Art of MicroRNA Research," Circulation Research, v.108:219-34.*
Iorio, et al. (2005) Cancer Research, v.65, No. 16, pp. 7065-7070.*
Lu, et al. (2005), Nature, v.435, pp. 834-838.*
Canadian Office Action, Application No. CA 2698771, dated Nov. 20, 2015.
Zhang et al., "MicroRNAs exhibit high frequency genomic alterations in human cancer", Proceedings of the National Academy of Sciences, USA, Jun. 2006, vol. 103, No. 24, pp. 9136-9141.

* cited by examiner

*Primary Examiner* — Jennifer McDonald
(74) *Attorney, Agent, or Firm* — MacMillan, sobanski & Todd, LLC

(57) ABSTRACT

Described herein are methods and compositions for the diagnosis, prognosis and treatment of ovarian cancer. Also described are methods of identifying anti-cancer agents.

1 Claim, 21 Drawing Sheets
(18 of 21 Drawing Sheet(s) Filed in Color)

| miR name | FDR | Ratio of geom means AZA/NT |
|---|---|---|
| hsa-mir-21 | 0.002013 | 4.277 |
| hsa-mir-203 | 0.0067368 | 3.826 |
| hsa-mir-146b | 0.0095114 | 2.968 |
| hsa-mir-205 | 0.0121302 | 2.877 |
| hsa-miR-30a-5p | 0.0160979 | 2.047 |
| hsa-miR-96 | 0.0161969 | 0.476 |
| hsa-mir-155 | 0.018638 | 1.784 |
| hsa-mir-383 | 0.018638 | 0.474 |
| hsa-miR-30c | 0.018638 | 2.286 |
| hsa-mir-193b | 0.018638 | 2.09 |
| hsa-mir-202 | 0.018638 | 1.782 |

CV Confusion Matrix
(Threshold=3.23866)

| True\Predicted | cancer | N | Class Error rate |
|---|---|---|---|
| cancer | 63 | 8 | 0.112676056 |
| N | 1 | 14 | 0.066666667 |

MISCLASSIFICATION ERROR = 0.11

| microRNAs | cancer score | N score |
|---|---|---|
| Hsa-mir-200c | 0.1152 | -0.5454 |
| Hsa-mir-200a | 0.1059 | -0.5012 |
| Hsa-mir-199a | -0.098 | 0.4637 |
| Hsa-mir-143 | -0.0946 | 0.4479 |
| Hsa-mir-199b | -0.0887 | 0.4197 |
| Hsa-mir-141 | 0.0874 | -0.4138 |
| Hsa-mir-145 | -0.0734 | 0.3473 |
| Hsa-mir-147 | -0.0679 | 0.3212 |
| Hsa-mir-133a | -0.0671 | 0.3176 |
| Hsa-mir-101 | -0.0616 | 0.2917 |
| Hsa-mir-214 | -0.0607 | 0.2873 |
| Hsa-mir-100 | -0.0535 | 0.2533 |
| Hsa-mir-140 | -0.0523 | 0.2474 |
| Hsa-mir-126 | -0.0501 | 0.2371 |
| Hsa-mir-224 | -0.0485 | 0.2294 |
| Hsa-mir-9 | -0.0481 | 0.2277 |
| Hsa-mir-105 | -0.0461 | 0.2184 |
| Hsa-mir-99a | -0.037 | 0.1753 |
| Hsa-mir-125a | -0.0315 | 0.1489 |
| Hsa-mir-211 | -0.0248 | 0.1174 |
| Hsa-mir-127 | -0.0232 | 0.11 |
| Hsa-mir-200b | 0.0179 | -0.0847 |
| Hsa-mir-125b-1 | -0.0177 | 0.0837 |
| Hsa-let-7c | -0.0152 | 0.0719 |
| Hsa-let-7d | -0.0138 | 0.0654 |
| Hsa-mir-124a | -0.0121 | 0.0574 |
| Hsa-mir-374 | -0.0119 | 0.0563 |
| Hsa-let-7a | -0.0113 | 0.0533 |
| Hsa-mir-134 | -0.0014 | 0.0068 |

Legend:
concordant
discordant
unchanged in Zhang study

FIG. 8 – Table 1

| microRNAs up-modulated | | | |
|---|---|---|---|
| | Score(d) | Fold Change | |
| hsa-miR-200a | 6.029559054 | 5.909228959 | concordant |
| miR-141 | 5.282215009 | 6.676969496 | discordant |
| hsa-miR-200c | 5.072214667 | 8.522477876 | unchanged in Zhang study |
| hsa-mir-200b | 3.833075725 | 3.305192114 | NA |
| hsa-miR-302b* | 2.735468464 | 7.576624548 | |
| hsa-miR-182 | 2.474388072 | 4.629588641 | |
| has-mir-325 | 2.427712097 | 3.582141857 | |
| has-mir-373 | 2.366832731 | 3.10378255 | |
| hsa-mir-203 | 2.106735098 | 3.924966016 | |
| hsa-mir-205 | 1.912402407 | 3.913918092 | |

| microRNAs down-modulated | | |
|---|---|---|
| | Score(d) | 1/Fold Change |
| hsa-mir-199a | -6.660234251 | 0.149170383 |
| hsa-mir-199b | -6.411673443 | 0.158503458 |
| hsa-mir-143 | -6.25941986 | 0.208966195 |
| hsa-mir-127 | -6.239314997 | 0.36263205 |
| hsa-mir-140 | -6.141381353 | 0.284933473 |
| hsa-mir-9 | -6.109935294 | 0.213902307 |
| hsa-mir-133a | -5.997775401 | 0.201323582 |
| hsa-mir-105 | -5.971698987 | 0.256386384 |
| hsa-mir-101 | -5.951436701 | 0.140368004 |
| hsa-mir-224 | -5.92099781 | 0.221057654 |
| hsa-mir-126 | -5.818430779 | 0.194310151 |
| hsa-mir-100 | -5.768583066 | 0.217155847 |
| hsa-mir-147 | -5.743104574 | 0.225260363 |
| hsa-mir-204 | -5.642915363 | 0.135983578 |
| hsa-mir-214 | -5.63781891 | 0.226868132 |
| hsa-mir-99a | -5.61022156 | 0.29031027 |
| hsa-mir-211 | -5.52630143 | 0.151341246 |
| hsa-mir-145 | -5.522715864 | 0.268284181 |
| hsa-let-7d | -5.353956412 | 0.292557531 |
| hsa-mir-124a | -5.308572049 | 0.30918176 |
| hsa-mir-125a | -5.275376888 | 0.285112062 |
| hsa-let-7c | -5.155238667 | 0.313348909 |
| hsa-let-7a | -5.043893498 | 0.346201662 |
| hsa-mir-29c | -4.992819698 | 0.284842858 |
| hsa-mir-195 | -4.880474865 | 0.333200438 |
| hsa-mir-125b | -4.706869872 | 0.319219655 |
| hsa-mir-374 | -4.625938602 | 0.260209699 |
| hsa-miR-302b | -4.540380253 | 0.26329528 |
| hsa-miR-29a | -4.538932739 | 0.330079052 |

FIG. 9 – Table 2

SEROUS VS NORMALS q value=0, fold change>3

Positive genes

| Gene Name | Score(d) | Fold Change |
|---|---|---|
| hsa-mir-200c | 4.874822 | 9.316226469 |
| hsa-mir-141 | 4.105882 | 6.297820292 |
| hsa-mir-200a | 5.22409 | 6.21082388 |
| hsa-mir-200b | 3.028617 | 3.354261291 |

Negative genes

| Gene Name | Score(d) | Fold Change |
|---|---|---|
| hsa-mir-137 | -4.79547 | 0.148869513 |
| hsa-mir-101 | -4.20173 | 0.156683391 |
| hsa-mir-199a | -4.95379 | 0.157135174 |
| hsa-mir-211 | -3.6933 | 0.159546591 |
| hsa-mir-204 | -4.35187 | 0.160197536 |
| hsa-mir-199b | -4.77294 | 0.169477272 |
| hsa-mir-101-1 | -4.61299 | 0.205344813 |
| hsa-mir-126 | -4.31991 | 0.205709452 |
| hsa-mir-224 | -4.51103 | 0.210351178 |
| hsa-mir-214 | -4.4747 | 0.211015924 |
| hsa-mir-143 | -4.66151 | 0.225560787 |
| hsa-mir-133a | -4.27006 | 0.22613586 |
| hsa-mir-147 | -4.19961 | 0.244193755 |
| hsa-mir-34c | -3.49226 | 0.244581699 |
| hsa-mir-100 | -4.031 | 0.244948271 |
| hsa-mir-302c | -2.7653 | 0.263419845 |
| hsa-mir-374 | -3.44084 | 0.264221816 |
| hsa-mir-9 | -4.22971 | 0.271871858 |
| hsa-mir-101 | -4.10703 | 0.281023282 |
| hsa-mir-125a | -3.96362 | 0.284404726 |
| hsa-mir-195 | -4.22039 | 0.288096703 |
| hsa-mir-29c | -3.81131 | 0.289651915 |
| hsa-mir-105 | -4.22771 | 0.290067186 |
| hsa-mir-145 | -4.16437 | 0.291445115 |
| hsa-let-7d | -3.95134 | 0.300703735 |
| hsa-mir-302b | -3.13456 | 0.30356362 |
| hsa-mir-9* | -3.40033 | 0.307833212 |
| hsa-mir-216 | -2.98653 | 0.309688574 |
| hsa-mir-99a | -4.06488 | 0.311194043 |
| hsa-mir-140 | -5.02723 | 0.313106918 |
| hsa-mir-125b-1 | -3.54736 | 0.314166789 |
| hsa-mir-215 | -3.62675 | 0.315298054 |
| hsa-let-7c | -3.8424 | 0.31529976 |
| hsa-mir-181a* | -3.69974 | 0.319272615 |
| hsa-mir-124a | -3.80122 | 0.320240298 |
| hsa-mir-28 | -2.56159 | 0.33142251 |
| hsa-let-7d | -3.80275 | 0.332028327 |
| hsa-mir-29a | -3.46281 | 0.333446637 |
| hsa-mir-133b | -2.68467 | 0.333883896 |

FIG. 10 - Table 3

ENDOMETRIOID VS NORMALS q value=0, fold change>3

Positive genes

| Gene Name | Score(d) | Fold Change | Score(d) | Fold Change |
|---|---|---|---|---|
| hsa-mir-200c | 5.602789 | 11.35184732 | 4.285621 | 5.169317934 |
| hsa-mir-141 | 6.66868 | 8.134845605 | 3.175124 | 4.632327322 |
| hsa-mir-200a | 5.873119 | 5.577590602 | 2.847984 | 5.089229918 |
| hsa-mir-205 | 4.091189 | 4.268810393 | 2.74905 | 3.473502434 |
| hsa-mir-21 | 3.308304 | 3.933420772 | 2.685224 | 2.25107383 |
| hsa-mir-182 | 3.336352 | 3.755931307 | 2.318534 | 2.000271165 |
| hsa-mir-200b | 3.822882 | 3.58677048 | 2.264066 | 2.501721471 |
| | | | 2.25371 | 2.455112892 |
| | | | 2.231062 | 2.385770368 |
| | | | 2.200151 | 3.904843321 |
| | | | 2.167726 | 2.263162617 |
| | | | 1.998298 | 2.69462407 |
| | | | 1.898917 | 2.611066113 |
| | | | 1.893946 | 2.183311521 |

Negative genes

| Gene Name | Score(d) | Fold Change |
|---|---|---|
| hsa-mir-302c | -4.5238 | 0.057739797 |
| hsa-mir-140 | -4.32451 | 0.122075074 |
| hsa-mir-101 | -4.28657 | 0.132249108 |
| hsa-mir-9 | -4.06022 | 0.165300935 |
| hsa-mir-147 | -5.31115 | 0.170117845 |
| hsa-mir-302b | -3.40316 | 0.177459541 |
| hsa-mir-9* | -3.96329 | 0.177591359 |
| hsa-mir-133a | -4.81939 | 0.1833621 |
| hsa-mir-137 | -2.7233 | 0.18888881 |
| hsa-mir-299-5p | -4.39191 | 0.192261887 |
| hsa-mir-105 | -4.82847 | 0.202341368 |
| hsa-mir-199b | -4.4869 | 0.209194024 |
| hsa-mir-199a | -4.52646 | 0.210975698 |
| hsa-mir-124a | -4.58559 | 0.214502778 |
| hsa-mir-100 | -4.17774 | 0.21482284 |
| hsa-mir-211 | -2.41054 | 0.240456539 |
| hsa-mir-224 | -3.8354 | 0.242984707 |
| hsa-mir-143 | -4.79084 | 0.249925609 |
| hsa-mir-126 | -3.76437 | 0.250497146 |
| hsa-mir-1 | -3.88978 | 0.271896204 |
| hsa-mir-7-2 | -2.91243 | 0.280749401 |
| hsa-mir-302a | -2.203 | 0.289793304 |
| hsa-mir-99a | -3.7768 | 0.294318696 |
| hsa-mir-216 | -1.97425 | 0.311440033 |
| hsa-mir-125b-1 | -3.72135 | 0.313838284 |
| hsa-let-7d | -3.92129 | 0.314438715 |
| hsa-let-7f | -4.38303 | 0.317245972 |
| hsa-mir-139 | -2.99323 | 0.32021126 |
| hsa-mir-125a | -3.54416 | 0.321469706 |
| hsa-mir-193 | -3.35024 | 0.3275396 |
| hsa-mir-144 | -2.56969 | 0.32905162 |
| hsa-mir-222 | -2.70438 | 0.330732291 |
| hsa-mir-323 | -5.14298 | 0.335905205 |
| hsa-mir-134 | -4.3392 | 0.336555522 |
| hsa-mir-370 | -3.40042 | 0.339804603 |

FIG. 10 cont - Table 3 cont

CLEAR CELL VS NORMALS q value=0, fold change>3

Positive genes

| Gene Name | Score(d) | Fold Change |
|---|---|---|
| hsa-mir-200c | 3.727262 | 8.735679382 |
| hsa-mir-200a | 4.251752 | 3.777659435 |

Negative genes

| Gene Name | Score(d) | Fold Change |
|---|---|---|
| hsa-mir-133a | -2.93133 | 0.088082129 |
| hsa-mir-140 | -2.97299 | 0.121810358 |
| hsa-mir-301 | -2.39538 | 0.123963114 |
| hsa-mir-137 | -2.27518 | 0.14653595 |
| hsa-mir-1 | -2.33148 | 0.147859091 |
| hsa-mir-9 | -2.98241 | 0.148568071 |
| hsa-mir-101 | -3.2276 | 0.166648407 |
| hsa-mir-100 | -3.83532 | 0.168061777 |
| hsa-mir-9* | -2.83792 | 0.174089614 |
| hsa-mir-199b | -3.67083 | 0.178632358 |
| hsa-mir-105 | -3.64152 | 0.196628255 |
| hsa-mir-98 | -3.50536 | 0.205661462 |
| hsa-mir-302a | -2.1459 | 0.211204706 |
| hsa-mir-199a | -3.56433 | 0.212611204 |
| hsa-mir-126 | -3.07167 | 0.22443264 |
| hsa-mir-125a | -3.94158 | 0.22469509 |
| hsa-mir-143 | -3.8477 | 0.229220021 |
| hsa-mir-19b | -2.84997 | 0.231739108 |
| hsa-mir-125b-1 | -3.97578 | 0.232452007 |
| hsa-mir-29a | -2.55383 | 0.236687361 |
| hsa-mir-147 | -3.22581 | 0.237154001 |
| hsa-mir-29c | -2.28388 | 0.243218229 |
| hsa-mir-222 | -2.5152 | 0.244824885 |
| hsa-mir-99a | -3.2997 | 0.25237176 |
| hsa-mir-224 | -3.01436 | 0.252667402 |
| hsa-mir-29b | -2.32129 | 0.25626224 |
| hsa-mir-18a | -1.87174 | 0.261229649 |
| hsa-mir-144 | -2.11054 | 0.263378069 |
| hsa-mir-100 | -3.22544 | 0.275300179 |
| hsa-mir-154 | -2.4008 | 0.278357698 |
| hsa-mir-302b | -1.87776 | 0.282435823 |
| hsa-mir-29b | -2.36214 | 0.284442159 |
| hsa-mir-125b | -3.37335 | 0.285579607 |
| hsa-let-7d | -3.39786 | 0.285818741 |
| hsa-let-7c | -3.1888 | 0.295568469 |
| hsa-mir-145 | -3.61294 | 0.297295886 |
| hsa-mir-181a* | -1.97299 | 0.29770489 |
| hsa-mir-19b | -2.24934 | 0.300862177 |
| hsa-mir-153 | -2.10042 | 0.300931686 |
| hsa-let-7d | -2.96829 | 0.332705239 |

MIXED VS NORMALS q value=0, fold change>3

Positive genes

| Gene Name | Score(d) | Fold Change |
|---|---|---|
| hsa-mir-200c | 4.94136514 | 13.03477954 |
| mir-182 | 4.75314464 | 8.234584867 |
| mir-141 | 6.52792749 | 8.114549554 |
| hsa-mir-200a | 8.59775165 | 6.749192792 |
| hsa-mir-205 | 3.15296179 | 6.612809032 |
| mir-203 | 3.95187923 | 6.023471984 |
| hsa-mir-200b | 4.21752758 | 4.559403288 |
| hsa-mir-302b* | 2.97964868 | 3.793211487 |
| hsa-mir-337 | 2.7911355 | 3.476209352 |

Negative genes

| Gene Name | Score(d) | Fold Change |
|---|---|---|
| hsa-mir-1 | -2.9664742 | 0.104268828 |
| hsa-mir-140 | -3.2747726 | 0.106318579 |
| hsa-mir-199a | -4.3900871 | 0.130723644 |
| hsa-mir-137 | -2.1620126 | 0.160523671 |
| hsa-mir-214 | -5.0278438 | 0.160582932 |
| hsa-mir-145 | -5.3314714 | 0.174664643 |
| hsa-mir-143 | -4.5203659 | 0.179176097 |
| hsa-mir-199b | -3.7977335 | 0.180079351 |
| hsa-mir-133a | -2.2671953 | 0.193349456 |
| hsa-mir-9 | -2.5636558 | 0.195399985 |
| hsa-mir-101 | -2.0553425 | 0.223886714 |
| hsa-mir-9* | -3.1666616 | 0.243634991 |
| hsa-mir-100 | -2.8720969 | 0.258813665 |
| hsa-mir-147 | -3.2823363 | 0.264405641 |
| hsa-mir-126 | -2.5427505 | 0.273636302 |
| hsa-mir-29c | -1.996995 | 0.287851362 |
| hsa-mir-134 | -4.3148185 | 0.293654878 |
| hsa-mir-34c | -2.1549977 | 0.29946464 |
| hsa-mir-10b | -2.9364249 | 0.303075071 |
| hsa-mir-125a | -3.2480671 | 0.305281943 |
| hsa-mir-224 | -2.5926058 | 0.305719687 |
| hsa-mir-105 | -2.6330954 | 0.316376728 |
| hsa-mir-181a* | -1.862744 | 0.321375183 |

FIG. 10 cont – Table 3 cont

| POORLY DIFFERENTIATED VS NORMALS | | |
|---|---|---|
| q value=0, fold change>2 | | |
| Positive genes | | |
| Gene Name | Score(d) | Fold Change |
| hsa-mir-325 | 4.285621 | 5.169317934 |
| hsa-mir-22 | 3.175124 | 4.632327322 |
| **hsa-miR-302c** | 2.847984 | 5.089229918 |
| hsa-miR-299-5p | 2.74905 | 3.473502434 |
| hsa-miR-373* | 2.685224 | 2.25107383 |
| hsa-miR-196b | 2.318534 | 2.000271165 |
| hsa-miR-194 | 2.264066 | 2.501721471 |
| hsa-mir-373 | 2.25371 | 2.455112892 |
| hsa-miR-324-3p | 2.231062 | 2.385770368 |
| hsa-miR-302b* | 2.200151 | 3.904843321 |
| hsa-mir-222 | 2.167726 | 2.263162617 |
| hsa-miR-105 | 1.998298 | 2.69462407 |
| hsa-miR-124a | 1.898917 | 2.611066113 |
| hsa-miR-1 | 1.893946 | 2.183311521 |

FIG. 10 cont - Table 3 cont

SEROUS VS ENDOMETRIOID

Positive genes

| Gene Name | Score(d) | Fold Change |
|---|---|---|
| hsa-miR-302b* | 2.1162067 | 4.562238026 |
| hsa-miR-325 | 1.957964 | 2.804324646 |
| hsa-miR-299-5p | 1.9831227 | 2.733850997 |
| hsa-miR-222 | 2.0673155 | 2.519055674 |
| hsa-miR-324-3p | 2.012373 | 2.40273827 |
| hsa-miR-196b | 2.222754 | 1.951149725 |
| hsa-miR-135b | 2.087203 | 1.817543895 |

Negative genes

| Gene Name | Score(d) | Fold Change |
|---|---|---|
| hsa-miR-212 | -2.533951 | 0.455394471 |
| hsa-miR-150 | -2.4778111 | 0.531181718 |

SEROUS VS NON-SEROUS

Positive genes

| Gene Name | Score(d) | Fold Change |
|---|---|---|
| hsa-miR-302b* | 1.8856931 | 2.387166664 |
| hsa-miR-22 | 1.8760835 | 2.289141433 |
| hsa-mir-373 | 1.9671527 | 2.026991587 |

Negative genes

| Gene Name | Score(d) | Fold Change |
|---|---|---|
| hsa-miR-148b | -1.9350385 | 0.473389 |
| hsa-miR-211 | -1.5246626 | 0.380840675 |

POORLY DIFFERENTIATED (PD) VS NON-PD

Negative genes

| Gene Name | Score(d) | Fold Change |
|---|---|---|
| hsa-mir-9 | -1.667661896 | 0.30496814 |
| hsa-mir-18 | -1.573399409 | 0.275779483 |

ENDOMETRIOID VS NON-ENDOMETRIOID

Positive genes

| Gene Name | Score(d) | Fold Change |
|---|---|---|
| hsa-miR-212 | 2.432924647 | 2.073840527 |

Negative genes

| Gene Name | Score(d) | Fold Change |
|---|---|---|
| hsa-miR-22 | -1.656798515 | 0.204982703 |
| hsa-miR-302b* | -2.041611412 | 0.248819032 |
| hsa-miR-299-5p | -2.034194437 | 0.341389128 |
| hsa-mir-325 | -2.065466938 | 0.357016955 |
| hsa-miR-194 | -1.727883478 | 0.378903888 |
| hsa-miR-101 | -1.785001084 | 0.379589721 |
| hsa-mir-373 | -1.696286422 | 0.387321213 |
| hsa-miR-324-3p | -1.977704757 | 0.424134141 |
| hsa-mir-222 | -1.783218284 | 0.42620566 |

CLEAR CELL VS NON-CLEAR CELL

Positive genes

| Gene Name | Score(d) | Fold Change |
|---|---|---|
| hsa-miR-30a-5p | 2.567858911 | 3.180690498 |
| hsa-miR-29b | 2.548556062 | 2.674746178 |
| hsa-miR-30e-5p | 2.090920369 | 2.632760423 |

Negative genes

| Gene Name | Score(d) | Fold Change |
|---|---|---|
| hsa-miR-20a | -2.08649871 | 0.408227411 |

FIG. 11 - Table 4

| LYMPHOVASCULAR INVASION | | | |
|---|---|---|---|
| | Negative genes | | |
| Gene Name | Score(d) | Fold Change | q-value(%) |
| hsa-mir-144 | -1.96 | 0.215959317 | 0 |
| hsa-mir-216 | -1.33255 | 0.41718005 | 0 |
| **OVARIAN SURFACE INVOLVEMENT** | | | |
| | Positive genes | | |
| Gene Name | Score(d) | Fold Change | q-value(%) |
| hsa-mir-101 | 2.018272 | 2.243033058 | 0 |
| hsa-miR-182* | 1.561247 | 2.065541993 | 0 |
| hsa-mir-22 | 1.401532 | 2.457950079 | 0 |
| hsa-miR-133a | 1.381055 | 3.450487913 | 0 |
| **TUBAL INVOLVEMENT** | | | |
| | Negative genes | | |
| Gene Name | Score(d) | Fold Change | q-value(%) |
| hsa-mir-137 | -1.9090693 | 0.37256783 | 0 |
| hsa-mir-101 | -1.7469971 | 0.390419388 | 0 |
| hsa-mir-215 | -1.4178719 | 0.324648273 | 0 |
| hsa-mir-211 | -1.1978493 | 0.407288227 | 0 |
| **PELVIC PERITONEUM** | | | |
| | Positive genes | | |
| Gene Name | Score(d) | Fold Change | q-value(%) |
| hsa-miR-302c | 1.150474 | 2.293373976 | 0 |
| **UTERUS INVOLVEMENT** | | | |
| | Positive genes | | |
| Gene Name | Score(d) | Fold Change | q-value(%) |
| hsa-mir-133a-2 | 1.27588177 | 3.266174858 | 0 |
| hsa-mir-143 | 1.91132897 | 2.362716504 | 0 |
| hsa-mir-145 | 1.82832273 | 2.282302908 | 0 |
| hsa-mir-1 | 1.57556619 | 2.278201035 | 0 |
| hsa-mir-147 | 0.99659977 | 2.115494772 | 0 |
| hsa-miR-126 | 1.36023908 | 2.08659655 | 0 |

FIG. 12 - Table 5

| miRs UP-modulated in ovarian carcinoma | CONFIRMED TARGET | EXPRESSION IN OVARIAN CARCINOMA | PUTATIVE TARGETS | EXPRESSION IN OVARIAN CARCINOMA |
|---|---|---|---|---|
| miR-200a | | | BAP1 | DOWN |
| | | | PDCD4 | down in other tumors |
| | | | GATA6 | DOWN |
| | | | VCAM-1 | DOWN |
| miR-200b | | | BAP1 | DOWN |
| | | | GATA4 | DOWN |
| | | | FN1 (fibronectin 1) | DOWN |
| miR-200c | | | BAP1 | DOWN |
| | | | FN1 (fibronectin 1) | DOWN |
| miR-141 | CLOCK (Kiriakidou M. Et al, 2004) | | BAP1 | DOWN |
| miRs DOWN-modulated in ovarian carcinoma | | | | |
| miR-140 | HDAC4 (Tuddenham L. et al, 2006) | UP | c-SRK | UP |
| | | | MMP13 | UP |
| | | | FGF2 | UP |
| miR-199a | | | CCNL1 | UP (other tumor types) |
| miR-199b | LAMC2 (Kiriakidou M. Et al, 2004) | UP (other cancers) | | |
| miR-145 | FLJ21308 (Kiriakidou M. Et al, 2004) | | | |
| miR-143 | ERK5 (Esau et al, 2004) | UP (other cancers) | COX-2 (strongly correlates with resistance to chemotherapy and poor outcome in ovarian cancer) | UP |
| miR-125a | ERBB2, ERBB3 (Scott et al, 2007) | UP | | |
| miR-125b | ERBB2, ERBB3 (Scott et al, 2007) | UP | | |
| miR-101 | Enx-1 (Lewis et al, 2003) | | COX-2 | UP |
| | MYCN (Lewis et al, 2003) | UP | | |
| miR-212 | | | WT1, BRCA1 | |
| miR-222 | c-KIT (Felli et al, 2005) | higher in high-grade compared with low-grade OSC | | |

FIG. 13 - Table 6

SEQUENCE LISTING

```
<160> NUMBER OF SEQ ID NOS: 98

<210> SEQ ID NO 1
<211> LENGTH: 22
<212> TYPE: RNA
<213> ORGANISM: Homo sapiens

<400> SEQUENCE: 1

uaacacuguc ugguaacgau gu                                                22


<210> SEQ ID NO 2
<211> LENGTH: 22
<212> TYPE: RNA
```

<213> ORGANISM: Homo sapiens

<400> SEQUENCE: 2
uaauacugcc ugguaaugau ga 22

<210> SEQ ID NO 3
<211> LENGTH: 23
<212> TYPE: RNA
<213> ORGANISM: Homo sapiens

<400> SEQUENCE: 3
uaauacugcc ggguaaugau gga 23

<210> SEQ ID NO 4
<211> LENGTH: 22
<212> TYPE: RNA
<213> ORGANISM: Homo sapiens

<400> SEQUENCE: 4
uaacacuguc ugguaaagau gg 22

<210> SEQ ID NO 5
<211> LENGTH: 22
<212> TYPE: RNA
<213> ORGANISM: Homo sapiens

<400> SEQUENCE: 5
acuuuaacau ggaagugcuu uc 22

<210> SEQ ID NO 6
<211> LENGTH: 24
<212> TYPE: RNA
<213> ORGANISM: Homo sapiens

<400> SEQUENCE: 6
uuuggcaaug guagaacuca cacu 24

<210> SEQ ID NO 7
<211> LENGTH: 23
<212> TYPE: RNA
<213> ORGANISM: Homo sapiens

<400> SEQUENCE: 7
ccuaguaggu guccaguaag ugu 23

<210> SEQ ID NO 8
<211> LENGTH: 23
<212> TYPE: RNA
<213> ORGANISM: Homo sapiens

<400> SEQUENCE: 8
gaagugcuuc gauuuugggg ugu 23

<210> SEQ ID NO 9
<211> LENGTH: 22
<212> TYPE: RNA
<213> ORGANISM: Homo sapiens

<400> SEQUENCE: 9
gugaaauguu uaggaccacu ag 22

<210> SEQ ID NO 10
<211> LENGTH: 22

-continued

<212> TYPE: RNA
<213> ORGANISM: Homo sapiens

<400> SEQUENCE: 10
uccuucauuc caccggaguc ug 22

<210> SEQ ID NO 11
<211> LENGTH: 23
<212> TYPE: RNA
<213> ORGANISM: Homo sapiens

<400> SEQUENCE: 11
cccaguguuc agacuaccug uuc 23

<210> SEQ ID NO 12
<211> LENGTH: 23
<212> TYPE: RNA
<213> ORGANISM: Homo sapiens

<400> SEQUENCE: 12
cccaguguuu agacuaucug uuc 23

<210> SEQ ID NO 13
<211> LENGTH: 21
<212> TYPE: RNA
<213> ORGANISM: Homo sapiens

<400> SEQUENCE: 13
ugagaugaag cacuguagcu c 21

<210> SEQ ID NO 14
<211> LENGTH: 22
<212> TYPE: RNA
<213> ORGANISM: Homo sapiens

<400> SEQUENCE: 14
cugaagcuca gagggcucug au 22

<210> SEQ ID NO 15
<211> LENGTH: 22
<212> TYPE: RNA
<213> ORGANISM: Homo sapiens

<400> SEQUENCE: 15
cagugguuuu acccuauggu ag 22

<210> SEQ ID NO 16
<211> LENGTH: 23
<212> TYPE: RNA
<213> ORGANISM: Homo sapiens

<400> SEQUENCE: 16
ucuuugguua ucuagcugua uga 23

<210> SEQ ID NO 17
<211> LENGTH: 22
<212> TYPE: RNA
<213> ORGANISM: Homo sapiens

<400> SEQUENCE: 17
uuuggucccc uucaaccagc ug 22

<210> SEQ ID NO 18

-continued

<211> LENGTH: 23
<212> TYPE: RNA
<213> ORGANISM: Homo sapiens

<400> SEQUENCE: 18
ucaaaugcuc agacuccugu ggu 23

<210> SEQ ID NO 19
<211> LENGTH: 21
<212> TYPE: RNA
<213> ORGANISM: Homo sapiens

<400> SEQUENCE: 19
uacaguacug ugauaacuga a 21

<210> SEQ ID NO 20
<211> LENGTH: 21
<212> TYPE: RNA
<213> ORGANISM: Homo sapiens

<400> SEQUENCE: 20
caagucacua gugguuccgu u 21

<210> SEQ ID NO 21
<211> LENGTH: 22
<212> TYPE: RNA
<213> ORGANISM: Homo sapiens

<400> SEQUENCE: 21
ucguaccgug aguaauaaug cg 22

<210> SEQ ID NO 22
<211> LENGTH: 22
<212> TYPE: RNA
<213> ORGANISM: Homo sapiens

<400> SEQUENCE: 22
aacccguaga uccgaacuug ug 22

<210> SEQ ID NO 23
<211> LENGTH: 20
<212> TYPE: RNA
<213> ORGANISM: Homo sapiens

<400> SEQUENCE: 23
guguguggaa augcuucugc 20

<210> SEQ ID NO 24
<211> LENGTH: 22
<212> TYPE: RNA
<213> ORGANISM: Homo sapiens

<400> SEQUENCE: 24
uucccuuugu cauccuaugc cu 22

<210> SEQ ID NO 25
<211> LENGTH: 22
<212> TYPE: RNA
<213> ORGANISM: Homo sapiens

<400> SEQUENCE: 25
acagcaggca cagacaggca gu 22

-continued

<210> SEQ ID NO 26
<211> LENGTH: 22
<212> TYPE: RNA
<213> ORGANISM: Homo sapiens

<400> SEQUENCE: 26
aacccguaga uccgaucuug ug 22

<210> SEQ ID NO 27
<211> LENGTH: 22
<212> TYPE: RNA
<213> ORGANISM: Homo sapiens

<400> SEQUENCE: 27
uucccuuugu cauccuucgc cu 22

<210> SEQ ID NO 28
<211> LENGTH: 23
<212> TYPE: RNA
<213> ORGANISM: Homo sapiens

<400> SEQUENCE: 28
guccaguuuu cccaggaauc ccu 23

<210> SEQ ID NO 29
<211> LENGTH: 22
<212> TYPE: RNA
<213> ORGANISM: Homo sapiens

<400> SEQUENCE: 29
agagguagua gguugcauag uu 22

<210> SEQ ID NO 30
<211> LENGTH: 20
<212> TYPE: RNA
<213> ORGANISM: Homo sapiens

<400> SEQUENCE: 30
uaaggcacgc ggugaaugcc 20

<210> SEQ ID NO 31
<211> LENGTH: 24
<212> TYPE: RNA
<213> ORGANISM: Homo sapiens

<400> SEQUENCE: 31
ucccugagac ccuuuaaccu guga 24

<210> SEQ ID NO 32
<211> LENGTH: 22
<212> TYPE: RNA
<213> ORGANISM: Homo sapiens

<400> SEQUENCE: 32
ugagguagua gguuguaugg uu 22

<210> SEQ ID NO 33
<211> LENGTH: 22
<212> TYPE: RNA
<213> ORGANISM: Homo sapiens

<400> SEQUENCE: 33
ugagguagua gguuguauag uu 22

<210> SEQ ID NO 34
<211> LENGTH: 22
<212> TYPE: RNA
<213> ORGANISM: Homo sapiens

<400> SEQUENCE: 34
uagcaccauu ugaaaucggu ua 22

<210> SEQ ID NO 35
<211> LENGTH: 21
<212> TYPE: RNA
<213> ORGANISM: Homo sapiens

<400> SEQUENCE: 35
uagcagcaca gaaauauugg c 21

<210> SEQ ID NO 36
<211> LENGTH: 22
<212> TYPE: RNA
<213> ORGANISM: Homo sapiens

<400> SEQUENCE: 36
ucccugagac ccuaacuugu ga 22

<210> SEQ ID NO 37
<211> LENGTH: 22
<212> TYPE: RNA
<213> ORGANISM: Homo sapiens

<400> SEQUENCE: 37
uuauaauaca accugauaag ug 22

<210> SEQ ID NO 38
<211> LENGTH: 23
<212> TYPE: RNA
<213> ORGANISM: Homo sapiens

<400> SEQUENCE: 38
uaagugcuuc cauguuuuag uag 23

<210> SEQ ID NO 39
<211> LENGTH: 22
<212> TYPE: RNA
<213> ORGANISM: Homo sapiens

<400> SEQUENCE: 39
uagcaccauc ugaaaucggu ua 22

<210> SEQ ID NO 40
<211> LENGTH: 22
<212> TYPE: RNA
<213> ORGANISM: Homo sapiens

<400> SEQUENCE: 40
uagcuuauca gacugauguu ga 22

<210> SEQ ID NO 41
<211> LENGTH: 24
<212> TYPE: RNA
<213> ORGANISM: Homo sapiens

<400> SEQUENCE: 41
uuuggcaaug guagaacuca cacu 24

-continued

<210> SEQ ID NO 42
<211> LENGTH: 22
<212> TYPE: RNA
<213> ORGANISM: Homo sapiens

<400> SEQUENCE: 42
accaucgacc guugauugua cc 22

<210> SEQ ID NO 43
<211> LENGTH: 22
<212> TYPE: RNA
<213> ORGANISM: Homo sapiens

<400> SEQUENCE: 43
uaaucucagc uggcaacugu ga 22

<210> SEQ ID NO 44
<211> LENGTH: 23
<212> TYPE: RNA
<213> ORGANISM: Homo sapiens

<400> SEQUENCE: 44
uaagugcuuc cauguuucag ugg 23

<210> SEQ ID NO 45
<211> LENGTH: 23
<212> TYPE: RNA
<213> ORGANISM: Homo sapiens

<400> SEQUENCE: 45
cagugcaaua guauugucaa agc 23

<210> SEQ ID NO 46
<211> LENGTH: 22
<212> TYPE: RNA
<213> ORGANISM: Homo sapiens

<400> SEQUENCE: 46
ugagguagua aguuguauug uu 22

<210> SEQ ID NO 47
<211> LENGTH: 23
<212> TYPE: RNA
<213> ORGANISM: Homo sapiens

<400> SEQUENCE: 47
ugugcaaauc caugcaaaac uga 23

<210> SEQ ID NO 48
<211> LENGTH: 23
<212> TYPE: RNA
<213> ORGANISM: Homo sapiens

<400> SEQUENCE: 48
uagcaccauu ugaaaucagu guu 23

<210> SEQ ID NO 49
<211> LENGTH: 23
<212> TYPE: RNA
<213> ORGANISM: Homo sapiens

<400> SEQUENCE: 49

-continued uaaggugcau cuagugcaga uag 23

<210> SEQ ID NO 50
<211> LENGTH: 22
<212> TYPE: RNA
<213> ORGANISM: Homo sapiens

<400> SEQUENCE: 50
uagguuaucc guguugccuu cg 22

<210> SEQ ID NO 51
<211> LENGTH: 23
<212> TYPE: RNA
<213> ORGANISM: Homo sapiens

<400> SEQUENCE: 51
ugugcaaauc uaugcaaaac uga 23

<210> SEQ ID NO 52
<211> LENGTH: 22
<212> TYPE: RNA
<213> ORGANISM: Homo sapiens

<400> SEQUENCE: 52
uugcauaguc acaaaaguga uc 22

<210> SEQ ID NO 53
<211> LENGTH: 20
<212> TYPE: RNA
<213> ORGANISM: Homo sapiens

<400> SEQUENCE: 53
uacaguauag augauguacu 20

<210> SEQ ID NO 54
<211> LENGTH: 21
<212> TYPE: RNA
<213> ORGANISM: Homo sapiens

<400> SEQUENCE: 54
agcuacaucu ggcuacuggg u 21

<210> SEQ ID NO 55
<211> LENGTH: 22
<212> TYPE: RNA
<213> ORGANISM: Homo sapiens

<400> SEQUENCE: 55
uggaauguaa agaaguaugu au 22

<210> SEQ ID NO 56
<211> LENGTH: 23
<212> TYPE: RNA
<213> ORGANISM: Homo sapiens

<400> SEQUENCE: 56
uaagugcuuc cauguuuugg uga 23

<210> SEQ ID NO 57
<211> LENGTH: 23
<212> TYPE: RNA
<213> ORGANISM: Homo sapiens

<400> SEQUENCE: 57
aggcagugua guuagcugau ugc 23

<210> SEQ ID NO 58
<211> LENGTH: 21
<212> TYPE: RNA
<213> ORGANISM: Homo sapiens

<400> SEQUENCE: 58
augaccuaug aauugacaga c 21

<210> SEQ ID NO 59
<211> LENGTH: 22
<212> TYPE: RNA
<213> ORGANISM: Homo sapiens

<400> SEQUENCE: 59
aaggagcuca cagucuauug ag 22

<210> SEQ ID NO 60
<211> LENGTH: 22
<212> TYPE: RNA
<213> ORGANISM: Homo sapiens

<400> SEQUENCE: 60
uuuggucccc uucaaccagc ua 22

<210> SEQ ID NO 61
<211> LENGTH: 22
<212> TYPE: RNA
<213> ORGANISM: Homo sapiens

<400> SEQUENCE: 61
ugguuuaccg ucccacauac au 22

<210> SEQ ID NO 62
<211> LENGTH: 23
<212> TYPE: RNA
<213> ORGANISM: Homo sapiens

<400> SEQUENCE: 62
uggaagacua gugauuuugu ugu 23

<210> SEQ ID NO 63
<211> LENGTH: 22
<212> TYPE: RNA
<213> ORGANISM: Homo sapiens

<400> SEQUENCE: 63
ucuacagugc acgugucucc ag 22

<210> SEQ ID NO 64
<211> LENGTH: 22
<212> TYPE: RNA
<213> ORGANISM: Homo sapiens

<400> SEQUENCE: 64
gccugcuggg guggaaccug gu 22

<210> SEQ ID NO 65
<211> LENGTH: 23
<212> TYPE: RNA
<213> ORGANISM: Homo sapiens

<400> SEQUENCE: 65
uuauugcuua agaauacgcg uag 23

<210> SEQ ID NO 66
<211> LENGTH: 22
<212> TYPE: RNA
<213> ORGANISM: Homo sapiens

<400> SEQUENCE: 66
auaaagcuag auaaccgaaa gu 22

<210> SEQ ID NO 67
<211> LENGTH: 22
<212> TYPE: RNA
<213> ORGANISM: Homo sapiens

<400> SEQUENCE: 67
ugagaacuga auuccauagg cu 22

<210> SEQ ID NO 68
<211> LENGTH: 22
<212> TYPE: RNA
<213> ORGANISM: Homo sapiens

<400> SEQUENCE: 68
uguaaacauc cucgacugga ag 22

<210> SEQ ID NO 69
<211> LENGTH: 23
<212> TYPE: RNA
<213> ORGANISM: Homo sapiens

<400> SEQUENCE: 69
uuuggcacua gcacauuuuu gcu 23

<210> SEQ ID NO 70
<211> LENGTH: 23
<212> TYPE: RNA
<213> ORGANISM: Homo sapiens

<400> SEQUENCE: 70
uuaaugcuaa ucgugauagg ggu 23

<210> SEQ ID NO 71
<211> LENGTH: 22
<212> TYPE: RNA
<213> ORGANISM: Homo sapiens

<400> SEQUENCE: 71
agaucagaag gugauugugg cu 22

<210> SEQ ID NO 72
<211> LENGTH: 23
<212> TYPE: RNA
<213> ORGANISM: Homo sapiens

<400> SEQUENCE: 72
uguaaacauc cuacacucuc agc 23

<210> SEQ ID NO 73
<211> LENGTH: 22
<212> TYPE: RNA
<213> ORGANISM: Homo sapiens

```
<400> SEQUENCE: 73

aacuggcccu caaagucccg cu                                              22

<210> SEQ ID NO 74
<211> LENGTH: 20
<212> TYPE: RNA
<213> ORGANISM: Homo sapiens

<400> SEQUENCE: 74

agagguauag ggcaugggaa                                                 20

<210> SEQ ID NO 75
<211> LENGTH: 22
<212> TYPE: RNA
<213> ORGANISM: Homo sapiens

<400> SEQUENCE: 75

ugugacuggu ugaccagagg gg                                              22

<210> SEQ ID NO 76
<211> LENGTH: 22
<212> TYPE: RNA
<213> ORGANISM: Homo sapiens

<400> SEQUENCE: 76

aggugguccg uggcgcguuc gc                                              22

<210> SEQ ID NO 77
<211> LENGTH: 21
<212> TYPE: RNA
<213> ORGANISM: Homo sapiens

<400> SEQUENCE: 77

gaacggcuuc auacaggagu u                                               21

<210> SEQ ID NO 78
<211> LENGTH: 23
<212> TYPE: RNA
<213> ORGANISM: Homo sapiens

<400> SEQUENCE: 78

uacccuguag aaccgaauuu gug                                             23

<210> SEQ ID NO 79
<211> LENGTH: 22
<212> TYPE: RNA
<213> ORGANISM: Homo sapiens

<400> SEQUENCE: 79

aagcugccag uugaagaacu gu                                              22

<210> SEQ ID NO 80
<211> LENGTH: 22
<212> TYPE: RNA
<213> ORGANISM: Homo sapiens

<400> SEQUENCE: 80

uagguaguuu ccuguuguug gg                                              22

<210> SEQ ID NO 81
<211> LENGTH: 22
<212> TYPE: RNA
```

<213> ORGANISM: Homo sapiens

<400> SEQUENCE: 81
uguaacagca acuccaugug ga 22

<210> SEQ ID NO 82
<211> LENGTH: 23
<212> TYPE: RNA
<213> ORGANISM: Homo sapiens

<400> SEQUENCE: 82 cgcaucccccu agggcauugg ugu 23

<210> SEQ ID NO 83
<211> LENGTH: 23
<212> TYPE: RNA
<213> ORGANISM: Homo sapiens

<400> SEQUENCE: 83
uauggcuuuu cauuccuaug uga 23

<210> SEQ ID NO 84
<211> LENGTH: 21
<212> TYPE: RNA
<213> ORGANISM: Homo sapiens

<400> SEQUENCE: 84
uaacagucuc cagucacggc c 21

<210> SEQ ID NO 85
<211> LENGTH: 22
<212> TYPE: RNA
<213> ORGANISM: Homo sapiens

<400> SEQUENCE: 85
ucucccaacc cuuguaccag ug 22

<210> SEQ ID NO 86
<211> LENGTH: 22
<212> TYPE: RNA
<213> ORGANISM: Homo sapiens

<400> SEQUENCE: 86
ucagugcauc acagaacuuu gu 22

<210> SEQ ID NO 87
<211> LENGTH: 22
<212> TYPE: RNA
<213> ORGANISM: Homo sapiens

<400> SEQUENCE: 87
uguaaacauc cuugacugga ag 22

<210> SEQ ID NO 88
<211> LENGTH: 23
<212> TYPE: RNA
<213> ORGANISM: Homo sapiens

<400> SEQUENCE: 88
uaaagugcuu auagugcagg uag 23

<210> SEQ ID NO 89
<211> LENGTH: 23

<212> TYPE: RNA
<213> ORGANISM: Homo sapiens

<400> SEQUENCE: 89
aacauucaac gcugucggug agu 23

<210> SEQ ID NO 90
<211> LENGTH: 22
<212> TYPE: RNA
<213> ORGANISM: Homo sapiens

<400> SEQUENCE: 90
ugagaacuga auuccauggg uu 22

<210> SEQ ID NO 91
<211> LENGTH: 22
<212> TYPE: RNA
<213> ORGANISM: Homo sapiens

<400> SEQUENCE: 91
ugggucuuug cgggcgagau ga 22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
probe

<400> SEQUENCE: 92
acatcgttac cagacagtgt ta 22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
probe

<400> SEQUENCE: 93
ccatctttac cagacagtgt ta 22

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
probe

<400> SEQUENCE: 94
gaacaggtag tctgaacact ggg 23

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
probe

<400> SEQUENCE: 95
tcacaagtta gggtctcagg ga 22

-continued

```
<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96

aagggattcc tgggaaaact ggac                                             24


<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97

gagacccagt agccagatgt agct                                             24


<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98

tcaacatcag tctgataagc ta                                               22
```

MICRORNA SIGNATURES IN HUMAN OVARIAN CANCER

CROSS-REFERENCE TO RELATED APPLICATIONS

This application is a continuation of U.S. Ser. No. 12/676,670 filed Mar. 31, 2010, which claims the benefit of PCT application PCT/US2008/075565 filed Sep. 8, 2008, which claims priority to U.S. Provisional Application No. 60/967,663, filed Sep. 6, 2007, the disclosures of which are expressly incorporated herein by reference.

GOVERNMENT SUPPORT

This invention was not made with any government support, and the government has no rights in this invention.

FIELD OF INVENTION

The present invention relates generally to the field of molecular biology. More particularly, it concerns methods and compositions involving microRNA (miRNAs or miRs) molecules. Methods and compositions for isolating, labeling, preparing miRNAs for analysis or as a tool for analysis are described, such as miRNA arrays. In addition, there are applications for miRNAs in diagnostics, therapeutics, and prognostics.

BACKGROUND OF THE INVENTION

Epithelial ovarian cancer is the most common gynecological malignancy and the sixth most common cancer in women worldwide, with highly aggressive natural history causing almost 125,000 deaths yearly. Despite advances in detection and cytotoxic therapies, only 30% of patients with advanced-stage ovarian cancer survive 5 years after initial diagnosis. The high mortality of this disease is mainly due to late stage diagnosis for more than 70% of ovarian cancers. In fact, when ovarian cancer is diagnosed in its early stage, that is still organ-confined, the five-year survival rate exceeds 90%. Unfortunately, only 19% of all ovarian cancers are diagnosed at this early stage. Indeed, this rather poor prognosis is due to (i) the insidious asymptomatic nature of this disease in its early onset, (ii) the lack of robust and minimally invasive methods for early detection, and (iii) tumor resistance to chemotherapy. The vast majority of human ovarian carcinomas are represented by ovarian epithelial cancers (OECs), deriving from the ovarian surface epithelium (OSE).

Ovarian adenocarcinomas occur as four major histological subtypes, serous, mucinous, endometrioid and clear cell, with serous being the most common. Current data indicate that each of these histological types is associated with distinct morphologic and molecular genetic alterations, but further investigations of the molecular mechanisms promoting ovarian cancer are necessary to determine how each of the subtypes emerges.

Over the last five years expression profiling technologies greatly improved, thus expanding the knowledge on cancer etiology and biomarkers with clinical applications. However, although these technologies have provided most of the new biomarkers with potential use for diagnosis, drug development, and tailored therapy, they have so far shed little insight into the detailed mechanisms at the origin of this neoplasia, thus suggesting that ovarian tumorigenesis may occur through novel or poorly characterized pathways.

A new class of small non-coding RNAs, named microRNAs, was recently discovered and shown to regulate gene expression at post-transcriptional level, for the most part by binding through partial sequence homology to the 3' untranslated region (3' UTR) of target mRNAs, and causing block of translation and/or mRNA degradation. MicroRNAs are 19-25 nt long molecules cleaved from 70-100 nt hairpin pre-miRNA precursors. The precursor is cleaved by cytoplasmic RNase III Dicer into ~22-nt miRNA duplex: one strand (miRNA*) of the short-lived duplex is degraded, while the other strand, that serves as mature miRNA, is incorporated into the RNA-induced silencing complex (RISC) and drives the selection of target mRNAs containing antisense sequences.

Several studies have demonstrated that miRNAs play important roles in essential processes, such as differentiation, cell growth and cell death.

Moreover, it has been shown that miRNAs are aberrantly expressed or mutated in cancers, suggesting that they may play a role as a novel class of oncogenes or tumor suppressor genes, depending on the targets they regulate: let-7, down-regulated in lung cancer, suppresses RAS and HMGA2 mir-15 and mir-16, deleted or down-regulated in leukemia, suppress BCL2; mir-17-5p and mir-20a control the balance of cell death and proliferation driven by the proto-oncogene c-Myc.

Clear evidences indicate that miRNA polycistron mir-17-92 acts as an oncogene in lymphoma and lung cancer; mir-372 and mir-373 are novel oncogenes in testicular germ cell tumors by numbing p53 pathway, miR-155, overexpressed in B cell lymphomas and solid tumors, leads to the development of B cell malignancies in an in vivo model of transgenic mice.

The use of microRNA microarray technologies has been used as a powerful tool to recognize microRNAs differentially expressed between normal and tumor samples, and also to identify miRNA expression signatures associated with well-defined clinico-pathological features and disease outcome. Several studies have also investigated the molecular mechanisms leading to an aberrant microRNAs expression, identifying the presence of genomic abnormalities in microRNA genes. More recently, few evidences have shown that microRNAs genes may be regulated also by epigenetic mechanisms, as changes in genomic DNA methylation pattern: miR-127 and miR-124a are transcriptionally inactivated by CpG island hypermethylation, while in lung cancer the overexpression of let-7a-3 seems to be due to DNA hypomethylation.

In spite of considerable research into therapies for ovarian cancer, ovarian cancer remains difficult to diagnose and treat effectively, and the mortality observed in patients indicates that improvements are needed in the diagnosis, treatment and prevention of the disease.

SUMMARY OF THE INVENTION

The present invention is based, in part, on the identification of an ovarian cancer-specific signature of miRNAs that are differentially-expressed in ovarian cancer cells, relative to normal control cells.

Accordingly, the invention encompasses methods of diagnosing whether a subject has, or is at risk for developing, ovarian cancer, comprising measuring the level of at least one miR in a test sample from the subject, wherein an alteration in the level of the miR in the test sample, relative to the level of a corresponding miR in a control sample, is indicative of the subject either having, or being at risk for developing, ovarian cancer.

In a particular aspect, there is provided herein a method of diagnosing whether a subject has, or is at risk for developing, ovarian cancer, comprising measuring the level of at least one miR in a test sample from the subject. An alteration in the level of the miR in the test sample, relative to the level of a corresponding miR in a control sample, is indicative of the subject either having, or being at risk for developing, ovarian cancer.

In another particular aspect, there is provided herein a method that includes identifying a correlation between miR expression and ovarian cancer or a predisposition for ovarian cancer, comprising: (a) labeling the miR isolated from a sample from a subject having or suspected of having a disease or condition; (b) hybridizing the miR to an miR array; (c) determining miR hybridization to the array; and (d) identifying miR differentially expressed in a sample representative of the disease or condition compared to a reference.

In a particular aspect, there is provided herein a method where identifying miR differentially expressed comprises generating an miR profile for the sample and evaluating the miR profile to determine whether miR in the sample are differentially expressed compared to a normal sample. In certain embodiments, the miR profile is selected from one or more of the miRs shown in Table 1. Also, in certain embodiments, the miR profile is selected from one or more of the miRs shown in FIG. 3A or FIG. 3B.

In a particular aspect, the ovarian cancer is one or more of clear cell, serous or endometrioid ovarian cancer. In a particular aspect, the miR profile is selected from one or more of the miRs shown in Table 3, whereby ovarian cancer cells are distinguished from normal cells. Also, in certain embodiments, the miR profile is selected from one or more of the miRs shown in Table 4, whereby ovarian cancer cells are distinguished by histotype among: serous, non-serous endometrioid, non-endometrioid, clear cell, non-clear cell, poorly differentiated and non-poorly differentiated.

In a particular embodiment, the miR profile involves at least one miR selected from the group consisting of miR-200a, miR-200b, miR-200c, miR-141, miR-199a, miR-140, miR-145 and miR-125b1, wherein a difference in expression of one or more of the miRNA compared to a normal sample is indicative of ovarian cancer. Also, in certain embodiments, the miR profile involves at least miR-200a, miR-200b, miR-200c, miR-141, miR-199a, miR-140, miR-145 and miR-125b1, wherein a difference in expression of one or more of the miR compared to a normal sample is indicative of ovarian cancer.

In a particular aspect, there is provided herein a method wherein an increase in expression of miR-200a, miR-200b, miR-200c or miR-141, and/or a decrease in expression of miR-199a, miR-140, miR-145 or miR-125b1, as compared to a normal sample, is indicative of ovarian cancer.

In a particular aspect, there is provided herein a method where the miR profile involves at least one miRNA selected from the group consisting of miR-200a, miR-200b, miR-200c and miR-141, wherein a difference in expression of one or more of the miRNA compared to a normal sample is indicative of serous ovarian cancer.

In a particular aspect, there is provided herein a method where the miR profile involves at least one miRNA selected from the group consisting of miR-205, miR-21, miR-182, miR-200b and miR-141, wherein a difference in expression of one or more of the miRNA compared to a normal sample is indicative of endometrioid ovarian cancer.

In a particular aspect, there is provided herein a method of distinguishing among ovarian cancer histotypes of serous, endometriod, clear cell and/or poorly differentiated ovarian cancer. In certain embodiments, the miR profile is selected from one or more of the miRs shown in FIG. 3A or FIG. 3B, and is indicative of serous ovarian cancer. In certain other embodiments, the miR profile is selected from one or more of the miRs shown in FIG. 3A or FIG. 3B, and is indicative of endometriod ovarian cancer. In certain other embodiments, the miR profile is selected from one or more of the miRs shown in FIG. 3A or FIG. 3B, and is indicative of clear cell ovarian cancer.

In a particular aspect, there is provided herein a method of inhibiting proliferation of an ovarian cancer cell comprising: i) introducing into the cell one or more agents which inhibit expression or activity of one or more miRs selected from the group shown in Table 3; ii) introducing into the cell one or more agents which enhances expression of one or more target genes of the miRs, or introducing into the cell a combination of the one or more agents of i) and ii), and maintaining the cells under conditions in which the one or more agents inhibits expression or activity of the miR, enhances expression or activity of one or more target genes of the miR, or results in a combination thereof, thereby inhibiting proliferation of the ovarian cancer cell. In a particular embodiment, the cell is a human cell.

In a particular aspect, there is provided herein a method where the expression of miR-200a, miR-200b, miR-200c and miR-141 are up-regulated, and have as common putative target the oncosuppressor BAP1, BRCA1-associated protein, that is down-modulated in ovarian cancer.

In a particular aspect, there is provided herein a method for modulating levels of one or more of miR-21, miR-203, miR-146, miR-205, miR-30-5p and miR-30c in an ovarian cancer cell compared with normal tissues, comprising administering an effective amount of a demethylation agent. In a particular embodiment, the levels are increased after 5-aza-2'-deoxycytidine demethylating treatment.

In a particular aspect, there is provided herein a method for altering expression of one or more of miR-21, miR-203, miR-146, miR-205, miR-30-5p and miR-30c, comprising controlling the DNA hypomethylation mechanism responsible for their overexpression.

The level of the at least one miR can be measured using a variety of techniques that are well known to those of skill in the art. In one embodiment, the level of the at least one miR is measured using Northern blot analysis. In another embodiment, the level of the at least one miR in the test sample is less than the level of the corresponding miR in the control sample. Also, in another embodiment, the level of the at least one miR in the test sample can be greater than the level of the corresponding miR in the control sample.

The invention also provides methods of diagnosing a cancer associated with one or more prognostic markers in a subject, comprising measuring the level of at least one miR in a cancer sample from the subject, wherein an alteration in the level of the at least one miR in the test sample, relative to the level of a corresponding miR in a control sample, is indicative of the subject having a cancer associated with the one or more prognostic markers. In one embodiment, the level of the at least one miR is measured by reverse transcribing RNA from a test sample obtained from the subject to provide a set of target oligodeoxynucleotides; hybridizing the target oligodeoxynucleotides to a microarray comprising miR-specific probe oligonucleotides to provide a hybridization profile for the test sample; and, comparing the test sample hybridization profile to a hybridization profile generated from a control sample. An alteration in the signal of at least one miR is indicative of the subject either having, or being at risk for developing, such cancer.

The invention also encompasses methods of treating cancer in a subject, wherein the signal of at least one miR, relative to the signal generated from the control sample, is de-regulated (e.g., down-regulated, up-regulated).

The invention also encompasses methods of diagnosing whether a subject has, or is at risk for developing, a cancer associated with one or more adverse prognostic markers in a subject, by reverse transcribing RNA from a test sample obtained from the subject to provide a set of target oligodeoxynucleotides; hybridizing the target oligodeoxynucleotides to a microarray comprising miR-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

The invention also encompasses methods of treating cancer in a subject who has a cancer in which at least one miR is down-regulated or up-regulated in the cancer cells of the subject relative to control cells. When the at least one miR is down-regulated in the cancer cells, the method comprises administering to the subject an effective amount of at least one isolated miR, such that proliferation of cancer cells in the subject is inhibited. When the at least one miR is up-regulated in the cancer cells, the method comprises administering to the subject an effective amount of at least one compound for inhibiting expression of the at least one miR, such that proliferation of cancer cells in the subject is inhibited.

In related embodiments, the invention provides methods of treating cancer in a subject, comprising: determining the amount of at least one miR in cancer cells, relative to control cells; and altering the amount of miR expressed in the cancer cells by: administering to the subject an effective amount of at least one isolated miR, if the amount of the miR expressed in the cancer cells is less than the amount of the miR expressed in control cells; or administering to the subject an effective amount of at least one compound for inhibiting expression of the at least one miR, if the amount of the miR expressed in the cancer cells is greater than the amount of the miR expressed in control cells, such that proliferation of cancer cells in the subject is inhibited.

The invention further provides pharmaceutical compositions for treating cancer, comprising at least one isolated miR and a pharmaceutically-acceptable carrier. In a particular embodiment, the pharmaceutical compositions the at least one isolated miR corresponds to a miR that is down-regulated in cancer cells relative to suitable control cells.

In another particular embodiment, the pharmaceutical composition comprises at least one miR expression inhibitor compound and a pharmaceutically-acceptable carrier. Also, in a particular embodiment, the pharmaceutical composition comprises at least one miR expression inhibitor compound is specific for a miR that is down regulated and/or up-regulated in cancer cells relative to suitable control cells.

In other embodiments, the present invention provides methods of identifying an anti-cancer agent, comprising providing a test agent to a cell and measuring the level of at least one miR associated with decreased expression levels in cancer cells, wherein an increase in the level of the miR in the cell, relative to a suitable control cell, is indicative of the test agent being an anti-cancer agent.

The present invention also provides methods of identifying an anti-cancer agent, comprising providing a test agent to a cell and measuring the level of at least one miR associated with increased expression levels in cancer cells, wherein an decrease in the level of the miR in the cell, relative to a suitable control cell, is indicative of the test agent being an anti-cancer.

In a specific aspect, as disclosed herein, at least one miR is selected the group shown in Table 3. In a particular embodiment the miR is selected from the group consisting of miR-200a, miR-141, miR-200c, and miR-200b, miR-199a, miR-140, miR-145, and miR-125b1.

In a specific aspect, there is also provided herein the identification of miRNAs whose expression is correlated with specific ovarian cancer biopathologic features, such as histotype, lymphovascular and organ invasion, and involvement of ovarian surface.

In another specific aspect, it is disclosed herein that the levels of miR-21, miR-203, and miR-205, up-modulated in ovarian carcinomas compared with normal tissues, were significantly increased after 5-aza-2'-deoxycytidine demethylating treatment of OVCAR3 cells.

In another particular aspect, there is also disclosed herein a method for altering the expression of these miRs by controlling the DNA hypomethylation mechanism responsible for their overexpression.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the United States Patent and Trademark Office upon request and payment of the necessary fee.

FIG. 1A: Tree generated by the hierarchical cluster analysis showing the separation of normal tissues from ovarian cancers on the basis of all human miRNAs spotted on the chip.

FIG. 1B: Some of the microRNAs most significantly down-modulated in tumors versus normal ovary.

FIG. 1C: The 4 microRNAs most significantly up-modulated in tumors versus normal ovary.

FIG. 3B, down-modulated).

FIG. 5A: Table reporting the most significant miRs differentially expressed resulting from the Microarray profiling.

FIG. 5B: Hierarchical cluster tree representation.

FIG. 5C: Real-Time PCR to verify the up-modulation of the 5 most significantly induced miRs, reported as graphical representation of miRs expression levels (each bar is an independent experiment resulting from the average of 3 technical replicates).

FIG. 5D: Northern Blot showing the up-modulation of miR-21 after treatment, normalized with EtBr gel staining.

FIG. 8: Table 1. PAM analysis of microRNAs differentially expressed between tumors and normals. Out of the 39 miRs found by SAM analysis, 29 miRs, 4 up-modulated and 25 down-modulated, were able to classify normal and tumor samples with a classification rate of 89%. The four miRs up-modulated were found amplified in the genomic study performed by Zhang et al., 2005; among the miRs down-modulated, 10 out of 25 were found deleted, 4 are discordant and 11 do not show any copy loss or gain in Zhang study.

FIG. 9—Table 2: miRs differentially expressed in tumors samples versus normal ovarian tissues. SAM analysis of microRNAs differentially expressed between tumors and normal tissues shows 10 microRNAs up-modulated and 29 down-modulated (q-value <1% and fold change >3). Out of 10 miRs up-modulated, 6 were found amplified in the genomic study performed by Zhang et al., 2005, and 4 did not show any copy loss or gain; among the miRs down-modulated, 12 out of 29 were found deleted, 6 are discordant and 11 do not show any copy loss or gain in Zhang study.

FIG. 10—Table 3: SAM analyses of different histological subtypes compared to the normal tissues.

FIG. 11—Table 4: SAM analyses of miRNA expression of different histotypes of tumors compared in pairs.

FIG. 12—Table 5: SAM analyses identifying microRNAs associated with EOC clinico-pathological features.

FIG. 13—Table 6: Table summarizing validated and the important predicted targets of the most significant microRNAs resulting from our analyses.

DETAILED DESCRIPTION OF THE PREFERRED EMBODIMENT

Figure 1A:
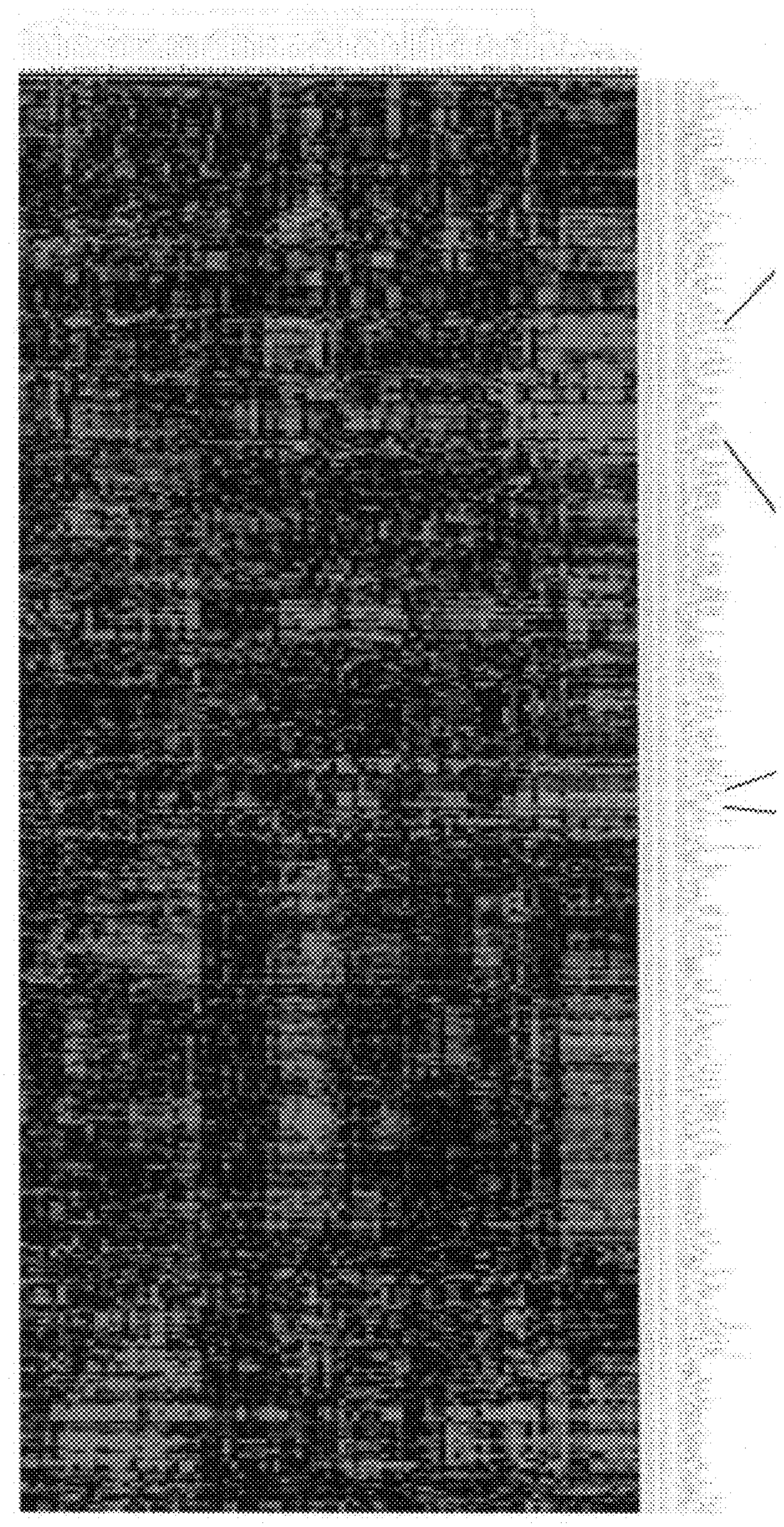
FIGS. 1A-1C: Cluster analysis of ovarian carcinomas and normal ovarian tissues.

The present invention is directed to compositions and methods relating to preparation and characterization of miRNAs, as well as use of miRNAs for therapeutic, prognostic, and diagnostic applications.

As used herein interchangeably, a "miR," "microRNA," "miR," or "miRNA" refers to the unprocessed or processed RNA transcript from an miR gene. As the miRs are not translated into protein, the term "miRs" does not include proteins. The unprocessed miR gene transcript is also called an "miR precursor," and typically comprises an RNA transcript of about 70-100 nucleotides in length. The miR precursor can be processed by digestion with an RNAse (for example, Dicer, Argonaut, or RNAse III, e.g., *E. coli* RNAse III)) into an active 19-25 nucleotide RNA molecule. This active 19-25 nucleotide RNA molecule is also called the "processed" miR gene transcript or "mature" miRNA. It is to be understood that the term "miR" as used herein can include one or more of miR-oligonucleotides, including mature miRs, pre-miRs, pri-miRs, or a miR seed sequence. In certain embodiments, a mixture of various miR nucleic acids can also be used. Also, in certain embodiments, the miRs may be modified to enhance delivery.

The miRNA (miR) information is available from the Sanger Institute, which maintains a registry of miRNA at http:/microrna.sanger.ac.uk/sequences/. The miRBase Sequence database includes the nucleotide sequences and annotations of published miRNA from a variety of sources. The miRBase Registry provides unique names for novel miRNA genes that comply with conventional naming nomenclature for new miRNA prior to publication. Also, the miRBase Targets is a resource for predicated miRNA targets in animals.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAase III). It is understood that the active 19-25 nucleotide RNA molecule can also be produced directly by biological or chemical synthesis, without having been processed from the miR precursor.

The present invention encompasses methods of diagnosing whether a subject has, or is at risk for developing, cancer, comprising measuring the level of at least one miR in a test sample from the subject and comparing the level of the miR in the test sample to the level of a corresponding miR in a control sample. As used herein, a "subject" can be any mammal that has, or is suspected of having, breast cancer. In a particular embodiment, the subject is a human who has, or is suspected of having, cancer.

The level of at least one miR can be measured in cells of a biological sample obtained from the subject. For example, a tissue sample can be removed from a subject suspected of having ovarian cancer associated with by conventional biopsy techniques. In another example, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR produced from a given miR gene in cells from the subject's sample can be compared to the corresponding miR levels from cells of the control sample.

An alteration (i.e., an increase or decrease) in the level of a miR in the sample obtained from the subject, relative to the level of a corresponding miR in a control sample, is indicative of the presence of cancer in the subject. In one embodiment, the level of the at least one miR in the test sample is greater than the level of the corresponding miR in the control sample (i.e., expression of the miR is "up-regulated"). As used herein, expression of a miR is "up-regulated" when the amount of miR in a cell or tissue sample from a subject is greater than the amount the same in a control cell or tissue sample. In another embodiment, the level of the at least one miR in the test sample is less than the level of the corresponding miR in the control sample (i.e., expression of the miR is "down-regulated"). As used herein, expression of an miR gene is "down-regulated" when the amount of miR produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, or the average level of miR gene expression previously obtained for a population of normal human controls.

The level of a miR in a sample can be measured using any technique that is suitable for detecting RNA expression levels in a biological sample. Suitable techniques for determining RNA expression levels in cells from a biological sample (e.g., Northern blot analysis, RT-PCR, in situ hybridization) are well known to those of skill in the art. In a particular embodiment, the level of at least one miR is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes for Northern blot hybridization of a given miR can be produced from the nucleic acid sequences of the given miR. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^{3}H$, $^{32}P$, $^{33}P$, $^{14}C$, or $^{35}S$; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^{8}$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR can be produced from the nucleic acid sequences.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). The methods for quantitative RT-PCR and variations thereof are within the skill in the art.

In some instances, it may be desirable to simultaneously determine the expression level of a plurality of different miRs in a sample. In other instances, it may be desirable to determine the expression level of the transcripts of all known miR genes correlated with a cancer. Assessing cancer-specific expression levels for hundreds of miR genes is time consuming and requires a large amount of total RNA (at least 20 μg for each Northern blot) and autoradiographic techniques that require radioactive isotopes.

To overcome these limitations, an oligolibrary, in microchip format (i.e., a microarray), may be constructed containing a set of probe oligodeoxynucleotides that are specific for a set of miR genes. Using such a microarray, the expression level of multiple microRNAs in a biological sample can be determined by reverse transcribing the RNAs to generate a set of target oligodeoxynucleotides, and hybridizing them to probe oligodeoxynucleotides on the microarray to generate a hybridization, or expression, profile. The hybridization profile of the test sample can then be compared to that of a control sample to determine which microRNAs have an altered expression level in cancer.

As used herein, “probe oligonucleotide” or “probe oligodeoxynucleotide” refers to an oligonucleotide that is capable of hybridizing to a target oligonucleotide.

“Target oligonucleotide” or “target oligodeoxynucleotide” refers to a molecule to be detected (e.g., via hybridization).

By “miR-specific probe oligonucleotide” or “probe oligonucleotide specific for an miR” is meant a probe oligonucleotide that has a sequence selected to hybridize to a specific miR, or to a reverse transcript of the specific miR.

An “expression profile” or “hybridization profile” of a particular sample is essentially a fingerprint of the state of the sample; while two states may have any particular gene similarly expressed, the evaluation of a number of genes simultaneously allows the generation of a gene expression profile that is unique to the state of the cell. That is, normal cells may be distinguished from cancer cells, and within cancer cells, different prognosis states (good or poor long term survival prospects, for example) may be determined. By comparing expression profiles of cancer cells in different states, information regarding which genes are important (including both up- and down-regulation of genes) in each of these states is obtained.

The identification of sequences that are differentially expressed in cancer cells or normal cells, as well as differential expression resulting in different prognostic outcomes, allows the use of this information in a number of ways. For example, a particular treatment regime may be evaluated (e.g., to determine whether a chemotherapeutic drug act to improve the long-term prognosis in a particular patient). Similarly, diagnosis may be done or confirmed by comparing patient samples with the known expression profiles. Furthermore, these gene expression profiles (or individual genes) allow screening of drug candidates that suppress the cancer expression profile or convert a poor prognosis profile to a better prognosis profile.

Accordingly, the invention provides methods of diagnosing whether a subject has, or is at risk for developing, cancer, comprising reverse transcribing RNA from a test sample obtained from the subject to provide a set of target oligodeoxynucleotides, hybridizing the target oligo-deoxynucleotides to a microarray comprising miRNA-specific probe oligonucleotides to provide a hybridization profile for the test sample, and comparing the test sample hybridization profile to a hybridization profile generated from a control sample, wherein an alteration in the signal of at least one miRNA is indicative of the subject either having, or being at risk for developing, cancer.

In one embodiment, the microarray comprises miRNA-specific probe oligonucleotides for a substantial portion of the human miRNome.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 μg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having cancer is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, i.e., noncancerous, control sample. An alteration in the signal is indicative of the presence of the cancer in the subject.

Other techniques for measuring miR gene expression are also within the skill in the art, and include various techniques for measuring rates of RNA transcription and degradation.

The invention also provides methods of diagnosing a cancer associated with one or more prognostic markers, comprising measuring the level of at least one miR in a cancer test sample from a subject and comparing the level of the at least one miR in the cancer test sample to the level of a corresponding miR in a control sample. An alteration (e.g., an increase, a decrease) in the signal of at least one miRNA in the test sample relative to the control sample is indicative of the subject either having, or being at risk for developing, cancer associated with the one or more prognostic markers.

The cancer can be associated with one or more prognostic markers or features, including, a marker associated with an adverse (i.e., negative) prognosis, or a marker associated with a good (i.e., positive) prognosis. In certain embodiments, the cancer that is diagnosed using the methods described herein is associated with one or more adverse prognostic features.

Particular microRNAs whose expression is altered in cancer cells associated with each of these prognostic markers are described herein. In one embodiment, the level of the at least one miR is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miRs in cells can result in the deregulation of one or more intended targets for these miRs, which can lead to the formation of cancer.

Therefore, altering the level of the miR (e.g., by decreasing the level of a miR that is up-regulated in CLL cells, by increasing the level of a miR that is down-regulated in cancer cells) may successfully treat the cancer. Examples of putative gene targets for miRNAs that are deregulated in cancer cells are described herein.

Accordingly, the present invention encompasses methods of treating cancer in a subject, wherein at least one miR is de-regulated (e.g., down-regulated, up-regulated) in the cancer cells of the subject. When the at least one isolated miR is down-regulated in the cancer cells, the method comprises administering an effective amount of the at least one isolated miR such that proliferation of cancer cells in the subject is inhibited. When the at least one isolated miR is up-regulated in the cancer cells, the method comprises administering to the subject an effective amount of at least one compound for inhibiting expression of the at least one miR gene, referred to herein as miR gene expression inhibition compounds, such that proliferation of cancer cells is inhibited.

The terms "treat", "treating" and "treatment", as used herein, refer to ameliorating symptoms associated with a disease or condition, for example, cancer, including preventing or delaying the onset of the disease symptoms, and/or lessening the severity or frequency of symptoms of the disease or condition. The terms "subject" and "individual" are defined herein to include animals, such as mammals, including but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR is an amount sufficient to inhibit proliferation of a cancer cell in a subject suffering from cancer. One skilled in the art can readily determine an effective amount of an miR to be administered to a given subject, by taking into account factors, such as the size and weight of the subject; the extent of disease penetration; the age, health and sex of the subject; the route of administration; and whether the administration is regional or systemic.

For example, an effective amount of an isolated miR can be based on the approximate or estimated body weight of a subject to be treated. Preferably, such effective amounts are administered parenterally or enterally, as described herein. For example, an effective amount of the isolated miR is administered to a subject can range from about 5 3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR to a given subject. For example, an miR can be administered to the subject once (e.g., as a single injection or deposition). Alternatively, an miR can be administered once or twice daily to a subject for a period of from about three to about twenty-eight days, more particularly from about seven to about ten days. In a particular dosage regimen, an miR is administered once a day for seven days. Where a dosage regimen comprises multiple administrations, it is understood that the effective amount of the miR administered to the subject can comprise the total amount of miR administered over the entire dosage regimen.

As used herein, an "isolated" miR is one which is synthesized, or altered or removed from the natural state through human intervention. For example, a synthetic miR, or an miR partially or completely separated from the coexisting materials of its natural state, is considered to be "isolated." An isolated miR can exist in substantially-purified form, or can exist in a cell into which the miR has been delivered. Thus, an miR which is deliberately delivered to, or expressed in, a cell is considered an "isolated" miR. An miR produced inside a cell from an miR precursor molecule is also considered to be "isolated" molecule.

Isolated miRs can be obtained using a number of standard techniques. For example, the miRs can be chemically synthesized or recombinantly produced using methods known in the art. In one embodiment, miRs are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miRs can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miRs in cancer cells.

The miRs that are expressed from recombinant plasmids can be isolated from cultured cell expression systems by standard techniques. The miRs which are expressed from recombinant plasmids can also be delivered to, and expressed directly in, the cancer cells. The use of recombinant plasmids to deliver the miRs to cancer cells is discussed in more detail below.

The miRs can be expressed from a separate recombinant plasmid, or they can be expressed from the same recombinant plasmid. In one embodiment, the miRs are expressed as RNA precursor molecules from a single plasmid, and the precursor molecules are processed into the functional miR by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which are incorporated herein by reference) and the *E. coli* RNAse III system (e.g., as described in U.S. Published Patent Application No. 2004/0014113 to Yang et al., the entire disclosure of which are incorporated herein by reference).

Selection of plasmids suitable for expressing the miRs, methods for inserting nucleic acid sequences into the plasmid to express the s, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miRs comprises a sequence encoding a miR precursor RNA under the control of the CMV intermediate-early promoter. As used herein, "under the control" of a promoter means that the nucleic acid sequences encoding the miR are located 3' of the promoter, so that the promoter can initiate transcription of the miR coding sequences.

The miRs can also be expressed from recombinant viral vectors. It is contemplated that the miRs can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miRs to cancer cells is discussed in more detail below.

The recombinant viral vectors of the invention comprise sequences encoding the miRs and any suitable promoter for expressing the RNA sequences. Suitable promoters include, for example, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miRs in a cancer cell.

Any viral vector capable of accepting the coding sequences for the miRs can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therap.* 2:301-310; Eglitis (1988), *Biotechniques* 6:608-614; Miller (1990), *Hum. Gene Therap.* 1:5-14; and Anderson (1998), *Nature* 392:25-30, the entire disclosures of which are incorporated herein by reference.

Particularly suitable viral vectors are those derived from AV and AAV. A suitable AV vector for expressing the miRs, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miRs, methods for constructing the recombinant AAV vector, and methods for delivering the vectors into target cells are described in Samulski et al. (1987), *J. Virol.* 61:3096-3101; Fisher et al. (1996), *J. Virol.,* 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miRs are expressed from a single recombinant AAV vector comprising the CMV intermediate early promoter.

In a certain embodiment, a recombinant AAV viral vector of the invention comprises a nucleic acid sequence encoding an miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound which inhibits miR expression can also be administered to the subject. As used herein, "inhibiting miR expression" means that the production of the active, mature form of miR after treatment is less than the amount produced prior to treatment. One skilled in the art can readily determine whether miR expression has been inhibited in a cancer cell, using for example the techniques for determining miR transcript level discussed above for the diagnostic method.

Inhibition can occur at the level of gene expression (i.e., by inhibiting transcription of a miR gene encoding the miR) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer associated with a cancer-associated chromosomal feature. One skilled in the art can readily determine an effective amount of an miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate or estimated body weight of a subject to be treated. Such effective amounts are administered parenterally or enterally, among others, as described herein. For example, an effective amount of the expression-inhibiting compound administered to a subject can range from about 5-3000 micrograms/kg of body weight, from about 700-1000 micrograms/kg of body weight, or it can be greater than about 1000 micrograms/kg of body weight.

One skilled in the art can also readily determine an appropriate dosage regimen for administering a compound that inhibits miR expression to a given subject. For example, an expression-inhibiting compound can be administered to the subject once (e.g., as a single injection or deposition). Alternatively, an expression-inhibiting compound can be administered once or twice daily to a subject for a period of from about three to about twenty-eight days, more preferably from about seven to about ten days. In a particular dosage regimen, an expression-inhibiting compound is administered once a day for seven days. Where a dosage regimen comprises multiple administrations, it is understood that the effective amount of the expression-inhibiting compound administered to the subject can comprise the total amount of compound administered over the entire dosage regimen.

Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR and destroy or induce the destruction of the target miR.

For example, expression of a given miR gene can be inhibited by inducing RNA interference of the miR gene with an isolated double-stranded RNA ("dsRNA") molecule which has at least 90%, for example at least 95%, at least 98%, at least 99% or 100%, sequence homology with at least a portion of the miR. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target miR.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miRs. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in an miR. The antisense nucleic acid can comprise a nucleic acid sequence that is 50-100% complementary, 75-100% complementary, or 95-100% complementary to a contiguous nucleic acid sequence in an miR. Nucleic acid sequences for the miRs are provided herein. Without wishing to be bound by any theory, it is believed that the antisense nucleic acids activate RNase H or another cellular nuclease that digests the miR/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miRs. Exemplary methods for producing and testing are within the skill in the art; see, e.g., Stein and Cheng (1993), *Science*

261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of an miR, and which is able to specifically cleave the miR. The enzymatic nucleic acid substrate binding region can be, for example, 50-100% complementary, 75-100% complementary, or 95-100% complementary to a contiguous nucleic acid sequence in an miR. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miRs. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR, or at least one compound for inhibiting miR expression, will inhibit the proliferation of cancer cells in a subject who has a cancer associated with a cancer-associated chromosomal feature. As used herein, to "inhibit the proliferation of a cancer cell" means to kill the cell, or permanently or temporarily arrest or slow the growth of the cell Inhibition of cancer cell proliferation can be inferred if the number of such cells in the subject remains constant or decreases after administration of the miRs or miR gene expression-inhibiting compounds. An inhibition of cancer cell proliferation can also be inferred if the absolute number of such cells increases, but the rate of tumor growth decreases.

The number of cancer cells in a subject's body can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The miRs or miR gene expression-inhibiting compounds can be administered to a subject by any means suitable for delivering these compounds to cancer cells of the subject. For example, the miRs or miR expression inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR or miR gene expression inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

An miR or miR gene expression inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and intravenous administration into the patient.

In the present methods, an miR or miR expression inhibiting compound can be administered to the subject either as naked RNA, in combination with a delivery reagent, or as a nucleic acid (e.g., a recombinant plasmid or viral vector) comprising sequences that express the miR or expression inhibiting compound. Suitable delivery reagents include, e.g., the Minis Transit TKO lipophilic reagent; lipofectin; lipofectamine; cellfectin; polycations (e.g., polylysine), and liposomes.

Recombinant plasmids and viral vectors comprising sequences that express the miRs or miR gene expression inhibiting compounds, and techniques for delivering such plasmids and vectors to cancer cells, are discussed herein.

In a particular embodiment, liposomes are used to deliver an miR or miR gene expression-inhibiting compound (or nucleic acids comprising sequences encoding them) to a subject. Liposomes can also increase the blood half-life of the s or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands which bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN) $BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miRs or miR gene expression inhibition compounds (or nucleic acids comprising sequences encoding them) to tumor cells.

The miRs or miR gene expression inhibition compounds can be formulated as pharmaceutical compositions, sometimes called "medicaments," prior to administering them to a subject, according to techniques known in the art. Accordingly, the invention encompasses pharmaceutical compositions for treating cancer. In one embodiment, the pharmaceutical compositions comprise at least one isolated miR and a pharmaceutically-acceptable carrier. In a particular embodiment, the at least one miR corresponds to a miR that has a decreased level of expression in cancer cells relative to suitable control cells.

In other embodiments, the pharmaceutical compositions of the invention comprise at least one miR expression inhibition compound. In a particular embodiment, the at least one miR gene expression inhibition compound is specific for a miR gene whose expression is greater in cancer cells than control cells.

Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is incorporated herein by reference.

The present pharmaceutical formulations comprise at least one miR or miR gene expression inhibition compound (or at least one nucleic acid comprising sequences encoding them) (e.g., 0.1 to 90% by weight), or a physiologically acceptable salt thereof, mixed with a pharmaceutically-acceptable carrier. The pharmaceutical formulations of the invention can also comprise at least one miR or miR gene expression inhibition compound (or at least one nucleic acid comprising sequences encoding them) which are encapsulated by liposomes and a pharmaceutically-acceptable carrier.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR or miR gene expression inhibition compound (or at least one nucleic acid comprising sequences encoding them) which is resistant to degradation by nucleases. One skilled in the art can readily synthesize nucleic acids which are nuclease resistant, for example by incorporating one or more ribonucleotides that are modified at the 2'-position into the miRs. Suitable 2'-modified ribonucleotides include those modified at the 2'-position with fluoro, amino, alkyl, alkoxy, and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR or miR gene expression inhibition compound (or at least one nucleic acid comprising sequences encoding them). A pharmaceutical composition for aerosol (inhalational) administration can comprise 0.01-20% by weight, preferably 1%-10% by weight, of the at least one miR or miR gene expression inhibition compound (or at least one nucleic acid comprising sequences encoding them) encapsulated in a liposome as described above, and a propellant. A carrier can also be included as desired; e.g., lecithin for intranasal delivery.

The invention also encompasses methods of identifying an anti-cancer agent, comprising providing a test agent to a cell and measuring the level of at least one miR in the cell. In one embodiment, the method comprises providing a test agent to a cell and measuring the level of at least one miR associated with decreased expression levels in cancer cells. An increase in the level of the miR in the cell, relative to a suitable control cell, is indicative of the test agent being an anti-cancer agent.

In other embodiments the method comprises providing a test agent to a cell and measuring the level of at least one miR associated with increased expression levels in cancer cells. A decrease in the level of the miR in the cell, relative to a suitable control cell, is indicative of the test agent being an anti-cancer agent.

Suitable agents include, but are not limited to drugs (e g, small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR (e.g., Northern blotting, in situ hybridization, RT-PCR, expression profiling) are also well known in the art.

The invention will now be illustrated by the following non-limiting examples. The following examples are intended to illustrate preferred embodiments of the invention and should not be interpreted to limit the scope of the invention as defined in the claims, unless so specified.

EXAMPLES

Presented herein are the results of a genome-wide miRNA expression profiling in a large set of normal and tumor ovarian tissues. It is now demonstrated here the existence of an ovarian cancer specific miRNA signature. Also, the altered methylation of microRNA genes is identified as a possible epigenetic mechanism responsible for their aberrant expression.

Materials and Methods

Ovarian Cancer Samples and Cell Lines.

A total of 84 snap-frozen normal and malignant ovarian tissues were collected at the GOG Tissues Bank, Columbus Children's Hospital, Columbus (OH, USA). The tissue collection used for microarray analysis included 15 normal ovarian tissue sections, and 69 malignant tissues, all ovarian epithelial carcinomas, including 31 serous (29 out of them showed a papillary pattern), 8 endometrioid, 4 clear cell, 9 poorly differentiated and 1 mucinous carcinomas. The ovarian cancer cell line IGROV1 was originally derived by Dr. Bernard (Institute Gustave Roussy, Villejuf, France), from a moderately differentiated ovarian carcinoma of an untreated patient, OAW-42 from Dr. Ulrich U. (Department of Obstetrics and Gynecology, University of Ulm, Germany), while OVCAR3, OVCAR8 and SK-OV3 were purchased from the American Type Culture Collection. All the cell lines were maintained in RPMI medium (Life Technologies, Rockville, Md.), supplemented with 10% (v/v) fetal bovine serum (FCS), 3 mM L-Glutamine and 100 U/ml penicillin/streptomycin.

miRNA Microarray Hybridization and Quantification

Total RNA isolation was performed with Trizol (Invitrogen, Carlsbad, Calif.) according to the manufacturer's instructions. RNA labeling and hybridization on microRNA microarray chips were performed as previously described (28) using 5 μg of total RNA from each sample. Hybridization was carried out on our microRNA microarray (Ohio State Comprehensive Cancer Center, version 2.0), which contains probes for 460 mature microRNAs spotted in quadruplicate (235 *homo sapiens,* 222 *mus musculus*, and three *Arabidopsis thaliana*) with annotated active sites. Often, more than one probe set exists for a given mature microRNA. Additionally, there are quadruplicate probes corresponding to most precursor microRNAs. Hybridization signals were detected with Streptavidin-Alexa647 conjugate and scanned images (Axon 4000B) were quantified using the Genepix 6.0 software (Axon Instruments, Sunnyvale, Calif.).

Computational Analysis of microRNA Microarray Data.

Microarray images were analyzed by using GENEPIX PRO. Average values of the replicate spots of each miRNA were background subtracted, normalized, and subjected to further analysis. We performed a global median normalization of Ovary microarray data by using BRB ArrayTools developed by Richard Simon & Amy Peng Lam (29). Absent calls were thresholded to 4.5 before subsequent statistical analysis. This level is the average minimum intensity level detected in the experiments. miRNA nomenclature was according to the Genome Browser (genome.ucsc.edu) and the miRNA database at Sanger Center (microrna.sanger.ac.uk/); in case of discrepancies the miRNA database was followed. Differentially expressed miRNAs were identified by using the t test procedure within significance analysis of microarrays (SAM), a method developed at Stanford University Labs based on recent paper of Tusher, Tibshirani and Chu (30).

To identify miRNA signatures we also applied PAM, which performs sample classification from gene expression data, via the "nearest shrunken centroid method" of Tibshirani, Hastie, Narasimhan and Chu (31).

Northern Blotting.

Northern blot analysis was performed as previously described. RNA samples (10 μg each) were run on 15% Polyacrylamide, 7M Urea Criterion pre-casted gels (Bio-Rad, Hercules, Calif.) and transferred onto Hybond-N+ membranes (Amersham, Piscataway, N.J.). The hybridization was performed at 370 C in ULTRAhyb-Oligo hybrization buffer (Ambion, Austin, Tex.) for 16 hours. Membranes were washed at 370 C, twice with 2×SSPE and 0.5% SDS.

The oligonucleotides used as probes were antisense to the sequence of the mature microRNAs (miR Registry at sanger.ac.uk/Software/Rfam/mirna/, which is fully incorporated herein by reference):

```
miR-200a:
                                    [SEQ ID NO: 92]
5' - ACA TCG TTA CCA GAC AGT GTT A -3';
```

-continued

```
miR-141:
                                        [SEQ ID NO: 93]
5'- CCA TCT TTA CCA GAC AGT GTT A - 3';

miR-199a:
                                        [SEQ ID NO: 94]
5'- GAA CAG GTA GTC TGA ACA CTG GG -3';

miR-125b1:
                                        [SEQ ID NO: 95]
5'TCA CAA GTT AGG GTC TCA GGG A -3';

miR-145:
                                        [SEQ ID NO: 96]
5'- AAG GGA TTC CTG GGA AAA CTG GAC -3';

miR-222:
                                        [SEQ ID NO: 97]
5'- GAG ACC CAG TAG CCA GAT GTA GCT -3';

miR-21:
                                        [SEQ ID NO: 98]
5'- TCA ACA TCA GTC TGA TAA GCT A -3'.
```

5S RNA or EtBr gel staining were used to normalize 200 ng of each probe was end labeled with 100 μCi [gamma-32P]-ATP using the polynucleotide kinase (Roche). Blots were stripped in boiling 0.1% SDS for 10 minutes before re-hybridization.

Real-Time PCR

The single tube TaqMan MicroRNA Assays were used to detect and quantify mature microRNAs on Applied Biosystems Real-Time PCR instruments in accordance with manufacturer's instructions (Applied Biosystems, Foster City, Calif.). Normalization was performed with 18S rRNA. All RT reactions, including no-template controls and RT minus controls, were run in a GeneAmp PCR 9700 Thermocycler (Applied Biosystems). Gene expression levels were quantified using the ABI Prism 7900HT Sequence detection system (Applied Biosystems). Comparative real-time PCR was performed in triplicate, including no-template controls. Relative expression was calculated using the comparative Ct method.

Demethylating Experiment

OVCAR3 cells were seeded at low density 48 h before treatment with 10 μM 5'aza-2'deoxycytidine (5'-AZA, Sigma). After 24 h of treatment, cells were collected and total RNA was isolated using Trizol reagent (Invitrogen). 3 replicates for both untreated cells and AZA-treated cells were used to evaluate the miR expression by Microarray profiling. Differentially expressed microRNAs were identified by using univariate two-classes T-test with random variance model.

Results

A microRNA Expression Signature Discriminates Ovarian Cancer Tissues from Normal Ovary.

A custom microarray platform already validated by numerous studies (19) was used to evaluate microRNA expression profiles on a heterogeneous set of ovarian tissues from different patients. This set included 15 normal ovarian samples, 69 ovarian malignant tumors, and 5 ovarian cancer cell lines, for a total of 89 biologically independent samples. Each tumor sample derived from a single specimen (data not shown).

Figure 1B:
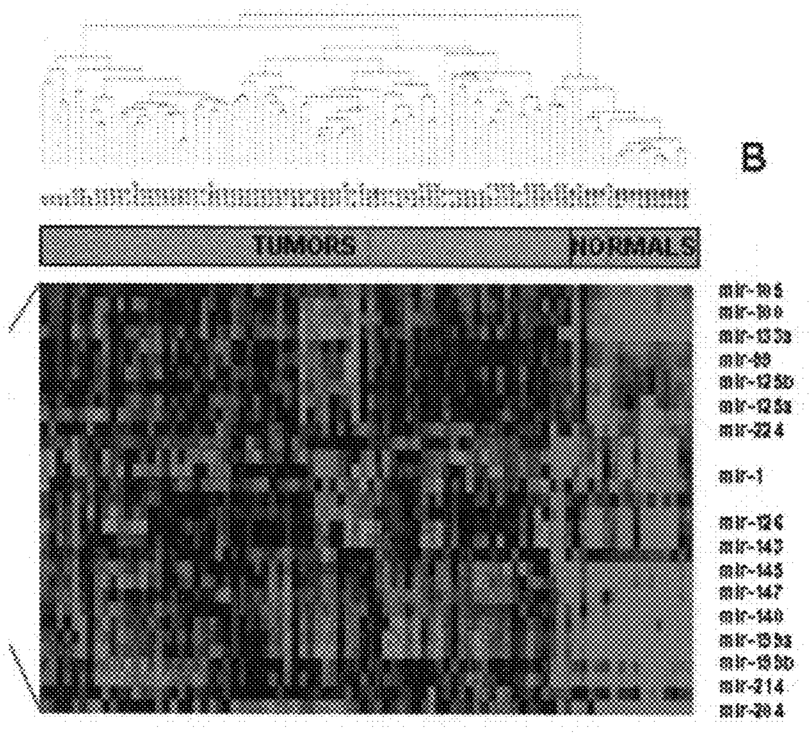
Figure 1C:
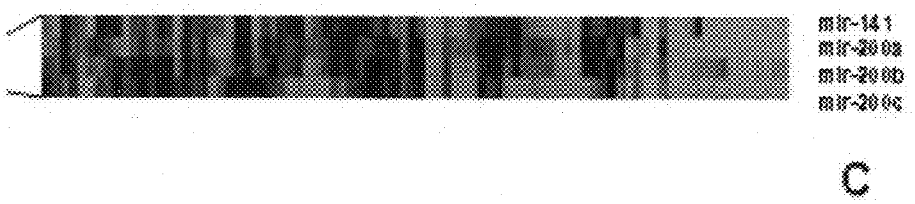

The unsupervised hierarchical clustering, based on all the human microRNAs spotted on the chip, generated a tree with a clear distinction of samples in two main groups, represented by normal tissues and malignant tissues (FIG. 1).

To identify microRNAs differentiating normal versus cancer tissue, we used SAM and PAM tools, and the results obtained from the two types of class prediction analysis were largely overlapping. The SAM comparison between normal and cancer tissues identified 39 miRNAs (with q-values <1% and fold changes >3) differentially expressed, 10 up-modulated in tumors and the remaining down-modulated (the list is reported in FIG. 9—Table 2).

Figure 6A:
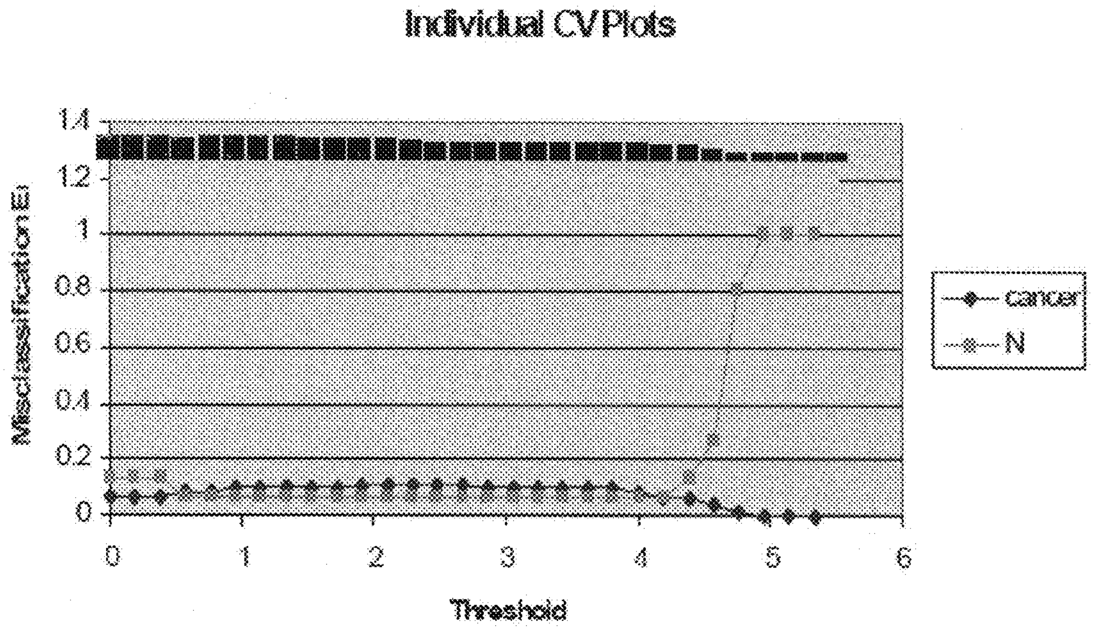
FIG. 6A and FIG. 6B: The PAM analysis displaying the graphical representation of the probabilities (0.0 to 1.0) of each sample for being a cancer or a normal tissue according to the miR signature reported in FIG. 8—Table 1, which describes a smaller set of 29 miRs, 4 up-modulated (miR-200a, miR-200b, miR-200c and miR-141) and 25 down-modulated (being miR-199a, miR-140, miR-145 and miR-125b1 among the most significant) differentiating normal versus tumor with a classification rate of 89%.
Figure 6B:
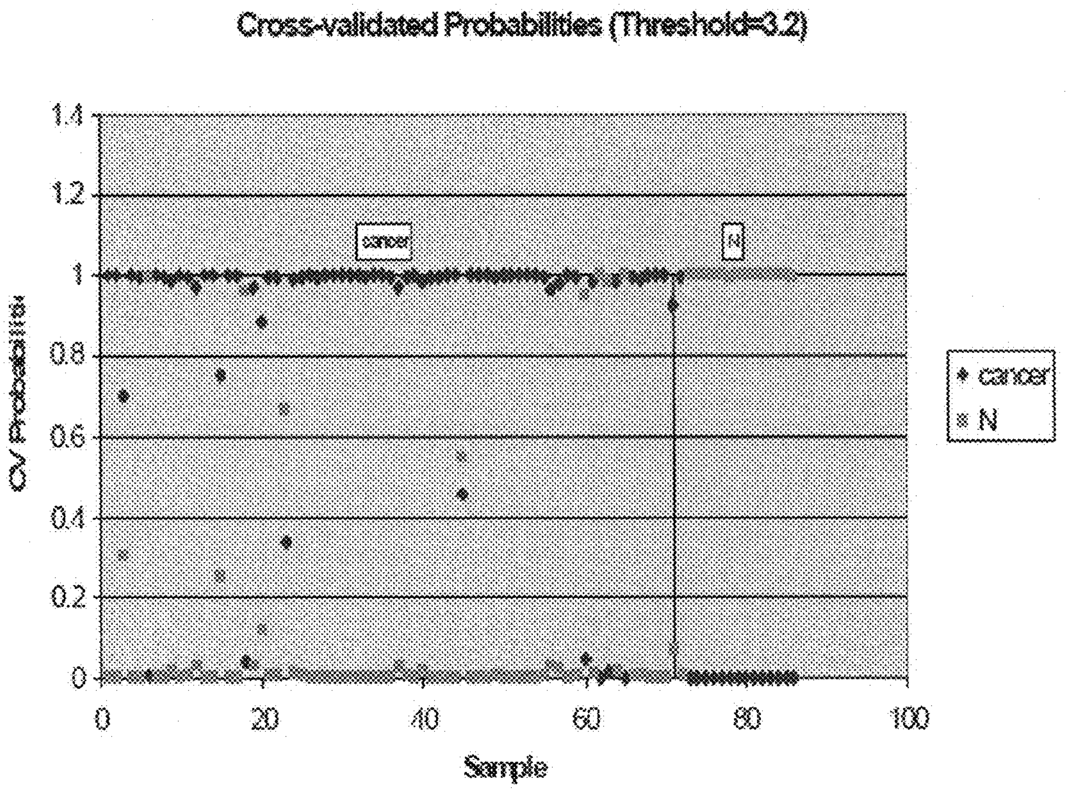

The PAM analysis in FIGS. 6A and 6B displays the graphical representation of the probabilities (0.0 to 1.0) of each sample for being a cancer or a normal tissue according to the miR signature reported in FIG. 8—Table 1, which describes a smaller set of 29 miRs, 4 up-modulated (miR-200a, -200b, -200c and -141) and 25 down-modulated (being miR-199a, miR-140, miR-145 and miR-125b1 among the most significant) differentiating normal versus tumor with a classification rate of 89%.

Figure 2A:
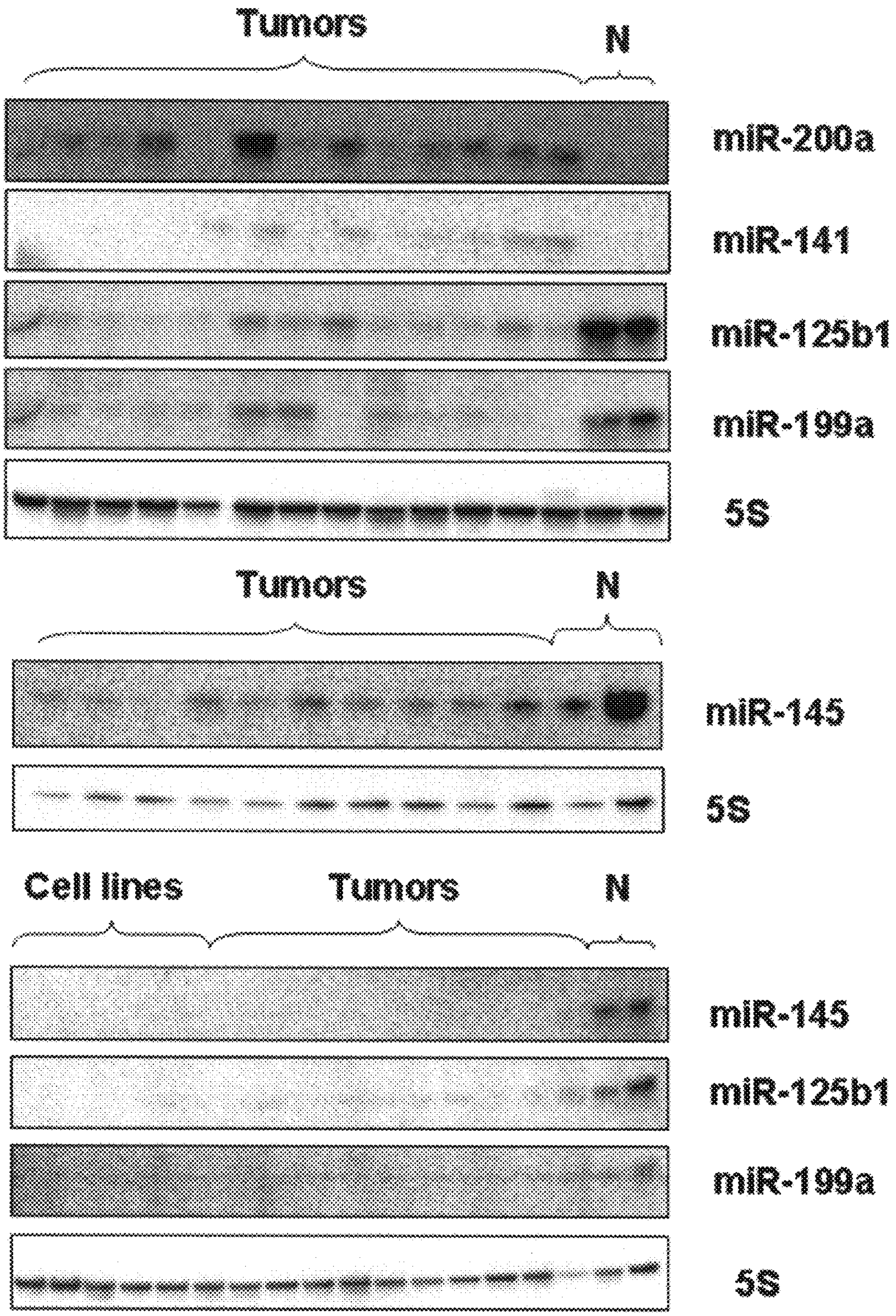
FIG. 2A: Northern blot analysis of human ovarian carcinomas with probes of miR-200a, miR-141, miR-199a, miF-125b1, miR-145. Evaluation of miR-199a, miR-125b1 and miR-145 on human ovarian cell lines. The 5S probe was used for normalization of expression levels in the different lanes.
Figure 2B:
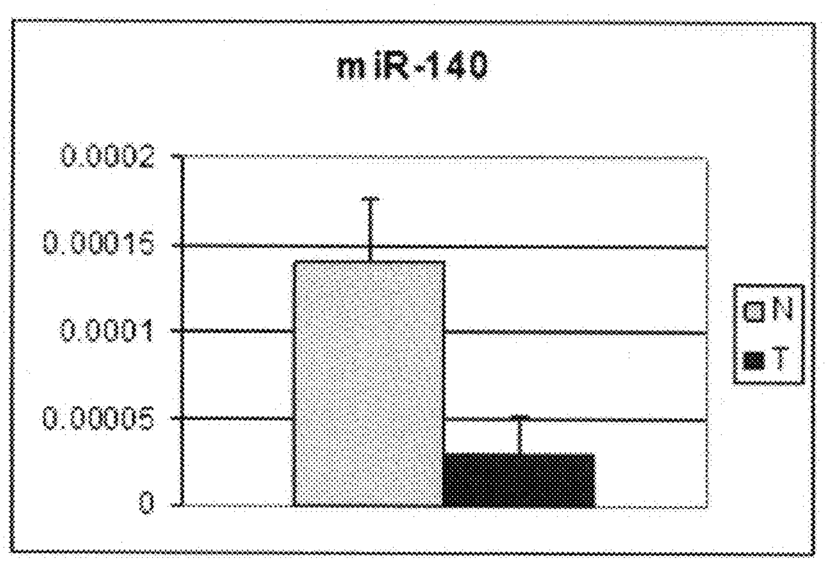
FIG. 2B: Real Time PCR to verify the miR-140 down-modulation in tumors compared to normal samples.

To confirm the results obtained by microarray analysis, we carried out Northern blots (FIG. 2A) or Real-Time PCR (FIG. 2B) on some of the differentially expressed microRNAs. We analyzed the expression of miR-200a and miR-141, the most significantly up-modulated in ovarian carcinoma, and the microRNAs most significantly down-modulated: miR-199a, miR-140, miR-145 and miR-125b1. All the experiments confirmed the results obtained by microarray analysis.

Bio-Pathological Features and microRNA Expression.

Figure 3A:
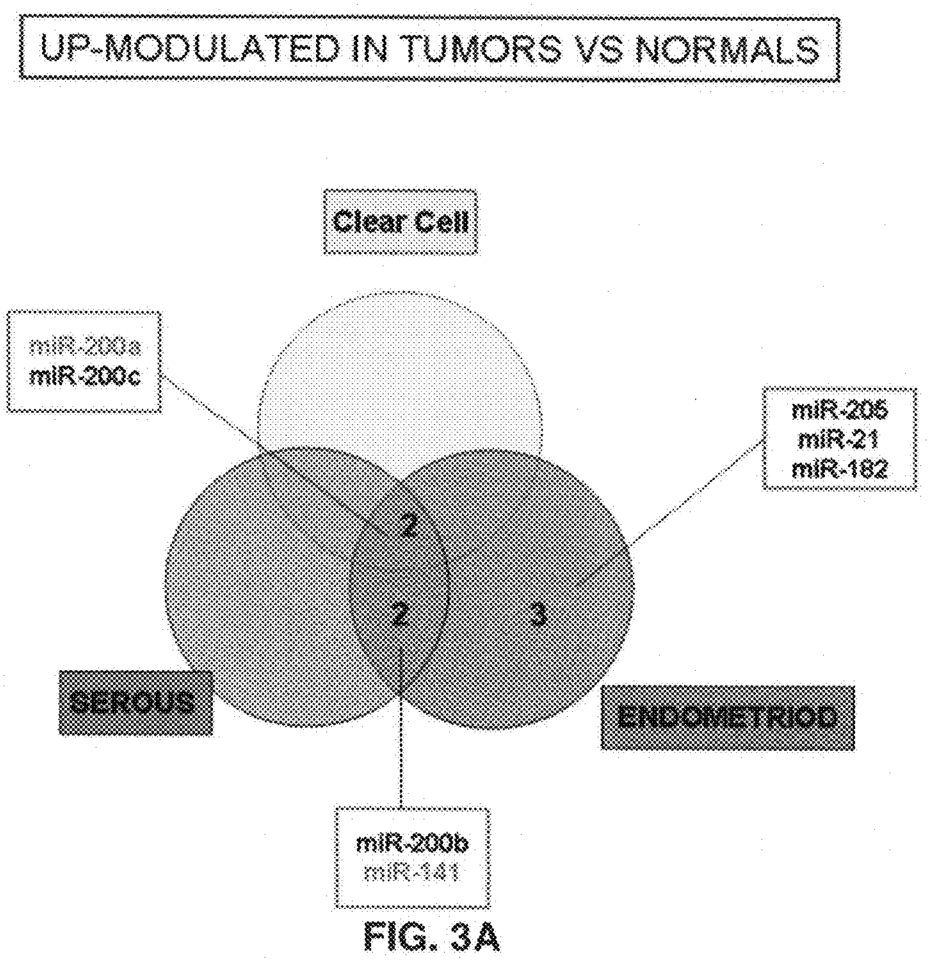
FIGS. 3A and 3B: Venn diagram showing the microRNA signatures characterizing different ovarian carcinoma histotypes (serous, endometrioid and clear cell) compared to the normal tissue (FIG. 3A, miRs up-modulated.
Figure 3B:
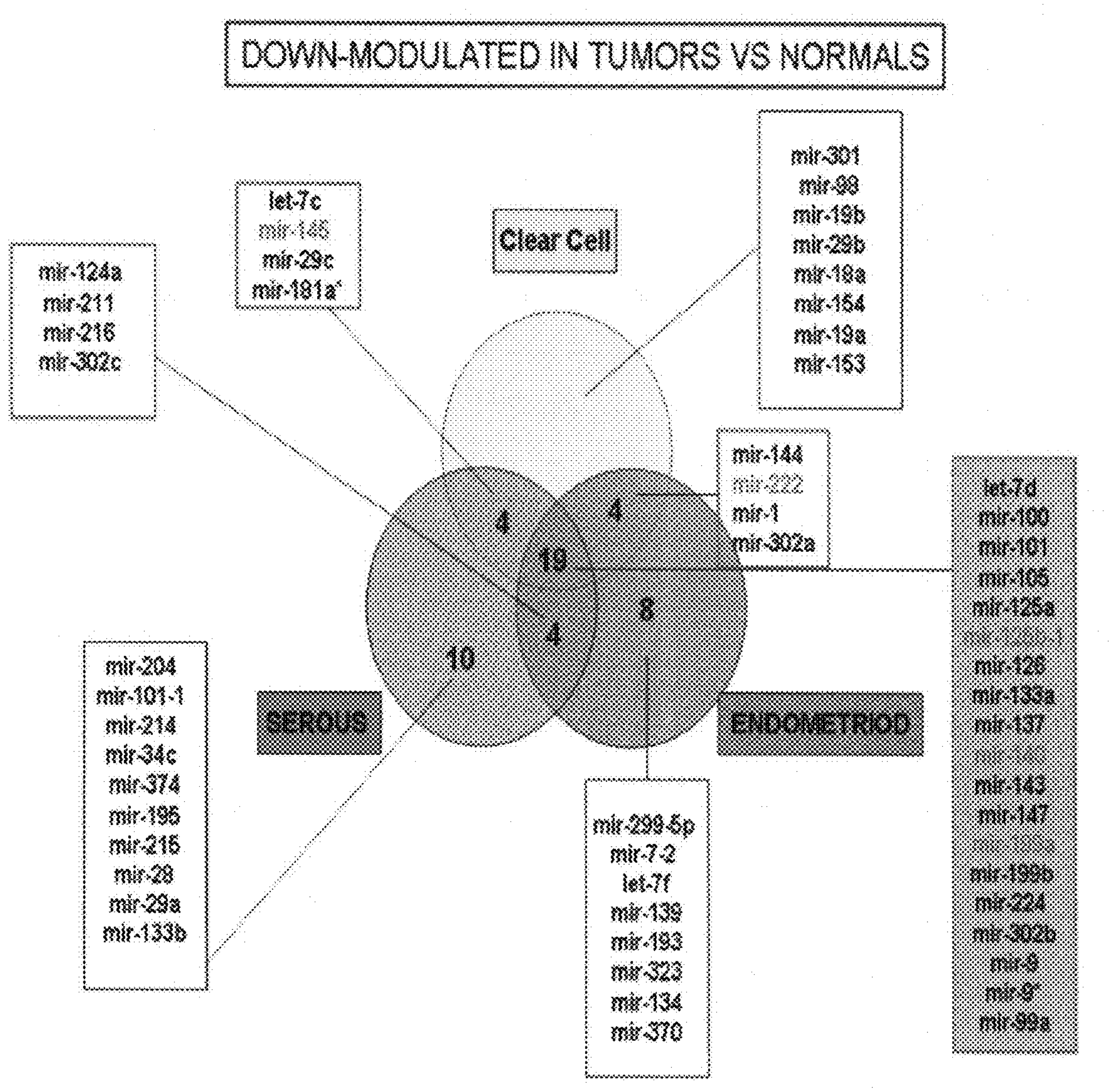

Considering that ovarian epithelial carcinomas occur as different histological subtypes characterized by distinct morphologic and molecular genetic alterations, we decided to compare the microRNA profile of each of them to the normal tissue to evaluate if microRNA expression profiles are different in distinct histotypes of ovarian carcinomas. Complete lists resulting from SAM analyses are reported in FIG. 10—Table 3, while a summary is shown in the Venn diagrams in FIGS. 3A and 3B:

Two (2) out of 4 microRNAs most significantly up-modulated (FIG. 3A) in tumors versus normal tissue, miR-200a and miR-200c, are up-modulated in all the three histotypes considered (serous, endometrioid and clear cell), while miR-200b and miR-141 up-modulation is shared by endometrioid and serous histotypes.

Moreover, the endometrioid histotype shows the up-modulation of 3 additional microRNAs, miR-21, miR-203 and miR-205. 19 miRs, including miR-125b1, miR-199a and miR-140, are down-modulated (FIG. 3B) in all the three histotypes examined in comparison with normal tissue, while 4 are shared in each paired analysis of the different signatures: miR-145, for example, is down-modulated in both serous and clear cell carcinomas; miR-222 in both endometrioid and clear cell carcinomas.

Considering the tumors classified as "mixed" and "poorly differentiated", we found that the first group revealed a signature with characteristics of different histotypes, sharing for example the overexpression of miR-200c and miR-181 with the endometrioid carcinomas, and the down-modulation of miR-214 with the serous, while the "poorly differentiated" tumors have a quite different pattern of microRNAs expression (FIG. 10—Table 3).

Figure 4A:
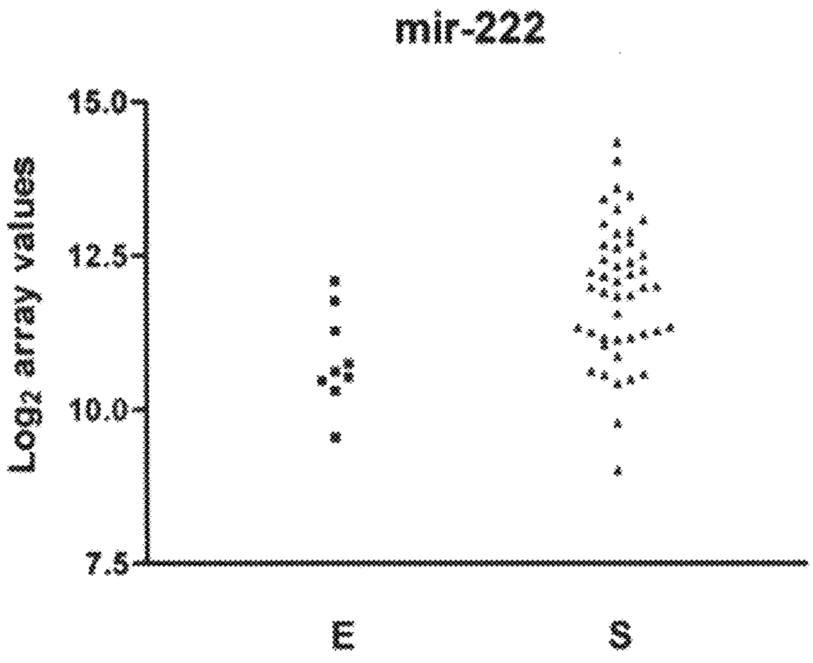
FIG. 4A: T-test graphic representation of miR-222 microarray data expression in serous and endometrioid tumors.

We then compared miRNA expression of different groups of tumors paired as reported in FIG. 11—Table 4, and in particular we compared the 2 most numerous histotypes, serous and endometriod. When considering the microRNAs differentially expressed in endometrioid carcinomas compared to serous, we found miR-212 up-modulated, and miR-302b* and miR-222 (T-test analysis of microarray data in FIG. 4A, $p<0.05$), among the microRNAs most significantly down-modulated.

Figure 4B:
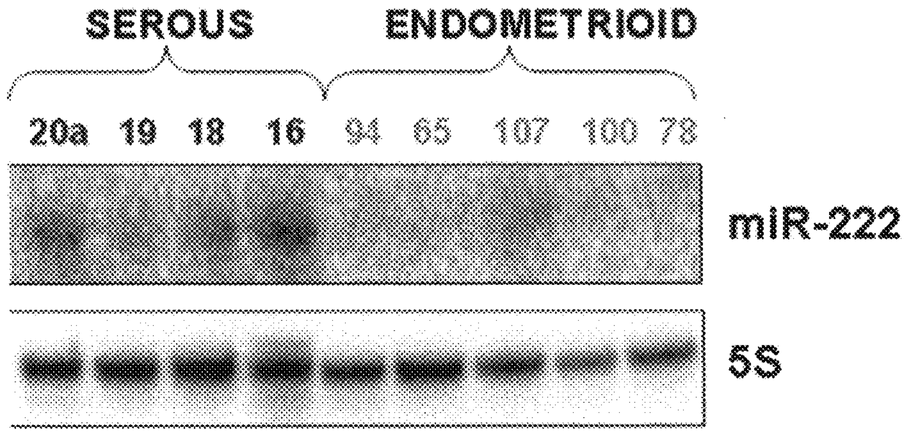
FIG. 4B: Verification by Northern Blot on a smallest set of samples.

In FIG. 4B a Northern Blot on a small set of samples verifies miR-222 overexpression in serous tumors compared to endometrioid. We then focused our attention on other clinico-pathological features associated with tumor specimens: while no miRs were found significantly differentially expressed in relation to the age of patients, other tumor characteristics seemed to affect miRs expression, such as lympho-vascular invasion, ovarian surface, tubal, uterus and pelvic peritoneum involvement (FIG. 12—Table 5).

To investigate if there were miRs associated with different Grade or Stage of the disease, we performed comparative analyses considering all the tumors or only the serous histotype, which was the most numerous, but we did not obtain any significant microRNA differentially expressed.

Confirmed and Potential Targets for miRNAs Members of Various Signatures.

Using the DianaTarbase at "diana.pcbi.upenn.edu/tarbase", we looked for confirmed targets of some of the most significant miRNAs resulting from our analyses, finding some interesting data: ERBB2 and ERBB3 receptors, for example, are targeted by miR-125 (32); miR-101, down-modulated in ovarian carcinoma, has been demonstrated targeting the oncogene MYCN (33). We then analyzed their potential targets using the "diana.pcbi.upenn.edu/miRGen" database, and evaluated for some of these molecules the expression levels in ovarian carcinoma. All the four most significantly up-modulated microRNAs, miR-200a, miR-200b, miR-200c and miR-141, for example, have as common putative target the oncosuppressor BAP1, BRCA1-associated protein, down-modulated in ovarian cancer. The information obtained is summarized in FIG. 13—Table 6.

Epigenetic Regulation of miRs Expression

Figures 5A, 5B:
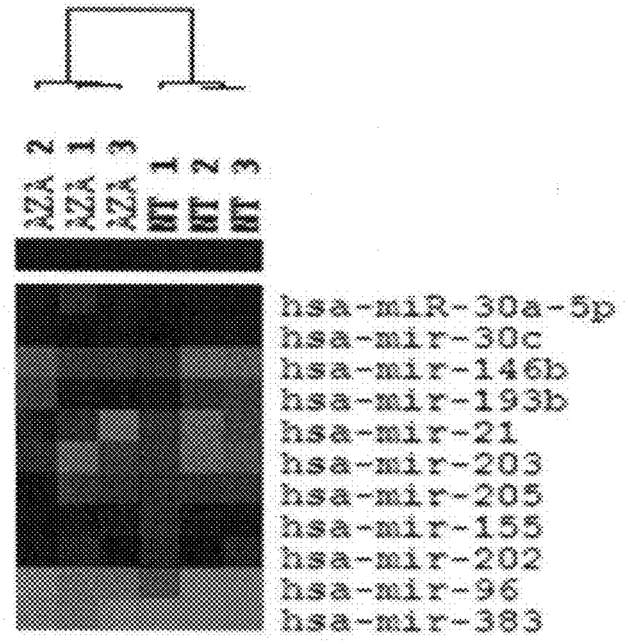
FIGS. 5A-5D: Expression pattern of microRNAs in OVCAR3 cell line before and after treatment with the demethylating agent 5'-AZA.

To evaluate if an aberrant DNA methylation pattern could also contribute to the altered microRNA expression characterizing the human ovarian carcinoma, we analyzed the miR profiling of the ovarian cell line OVCAR3, before and after treatment with the demethylating agent 5-Aza-2'-deoxycitidine. The analysis of Micro array data showed 11 human microRNAs differentially expressed, 9 up-modulated and 2 down-modulated (significance threshold of each univariate test: $p<0.001$), being miR-21, miR-203, miR-146b, miR-205, miR-30-5p and miR-30c the most significant induced upon treatment (the miRs differentially expressed are listed in FIG. 5A, while the resulting hierarchical cluster tree is reported in FIG. 5B).

Figure 5C:
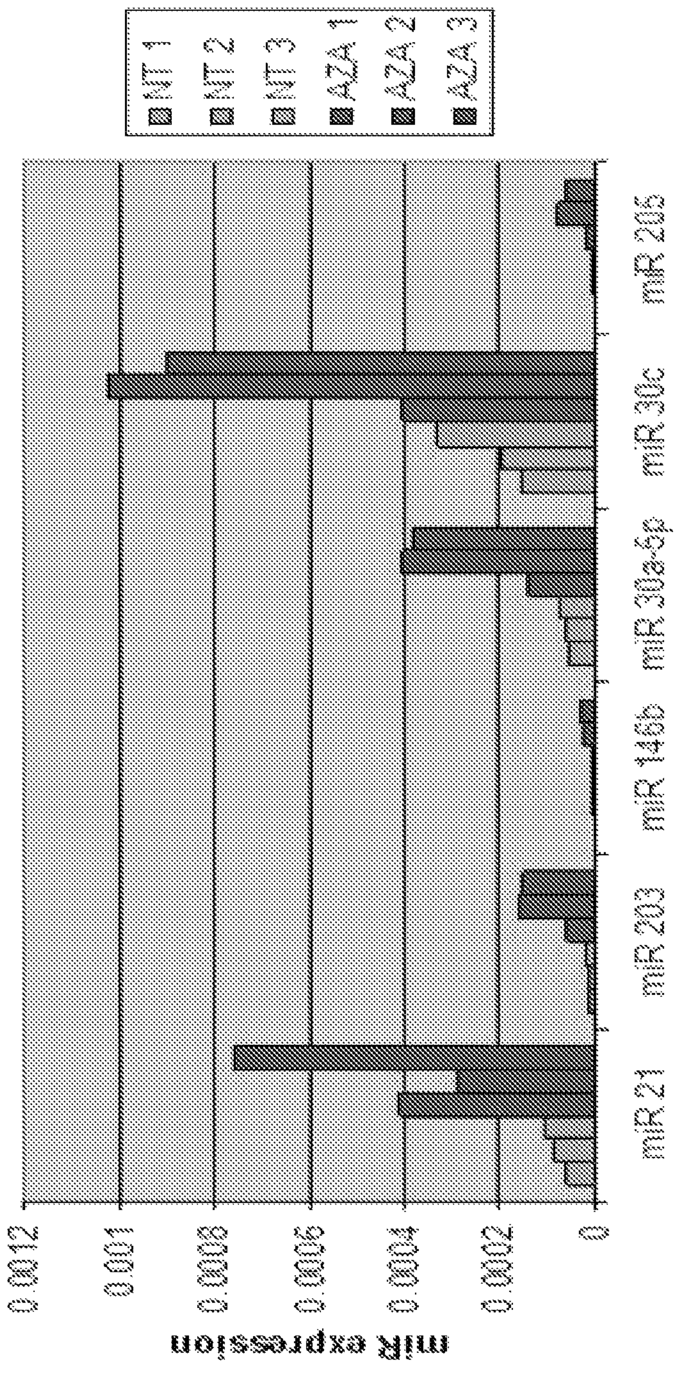
Figure 5D:
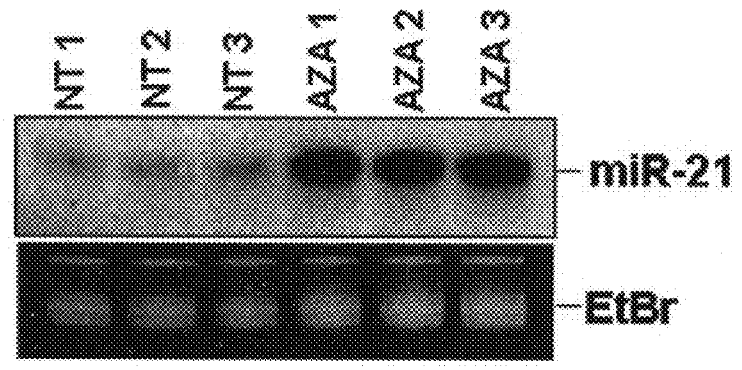

Real-Time PCRs to verify the up-modulation of the 5 most significantly induced miRs are described in FIGS. 5C and 5D as graphical representation of miR expression levels (FIG. 5C), and miR-21 was also validated by Northern Blot (FIG. 5D).

Figure 7A:
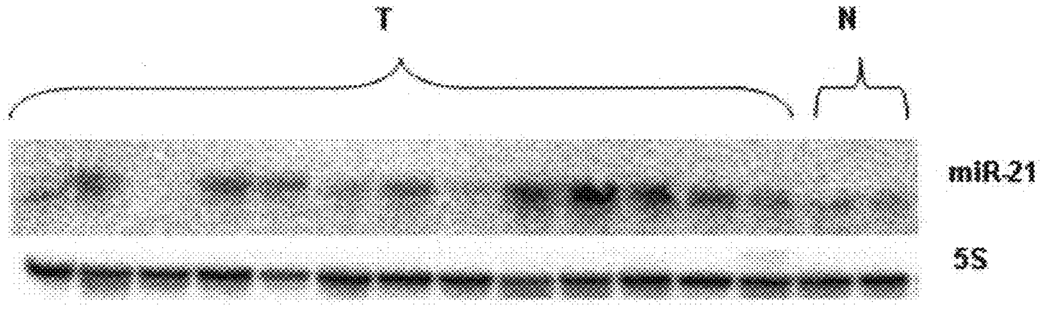
FIG. 7A and FIG. 7B: Northern Blotting (FIG. 7A) on a panel of human ovarian carcinomas and two normal tissues; miR-21 and miR-203 are associated with CpG islands, being the miR-203 embedded in a CpG island 875 bp long, and the miR-21 characterized by a CpG island −2 kb upstream the mature sequence (FIG. 7B), while miR-205 does not show any CpG island in a region spanning 2 Kb upstream its mature form.
Figure 7B:
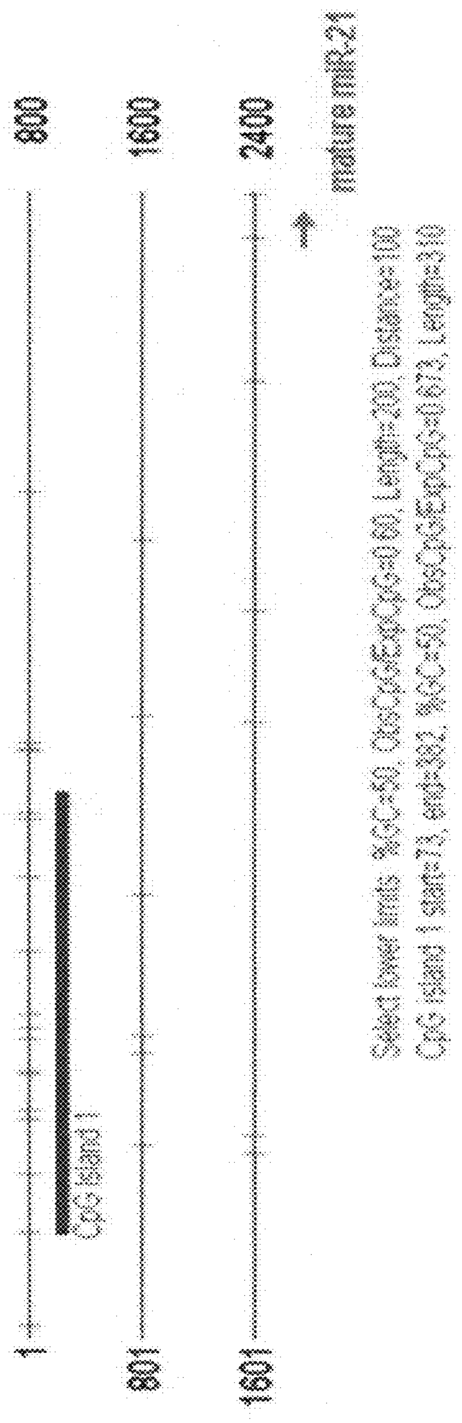
Figure 7B:
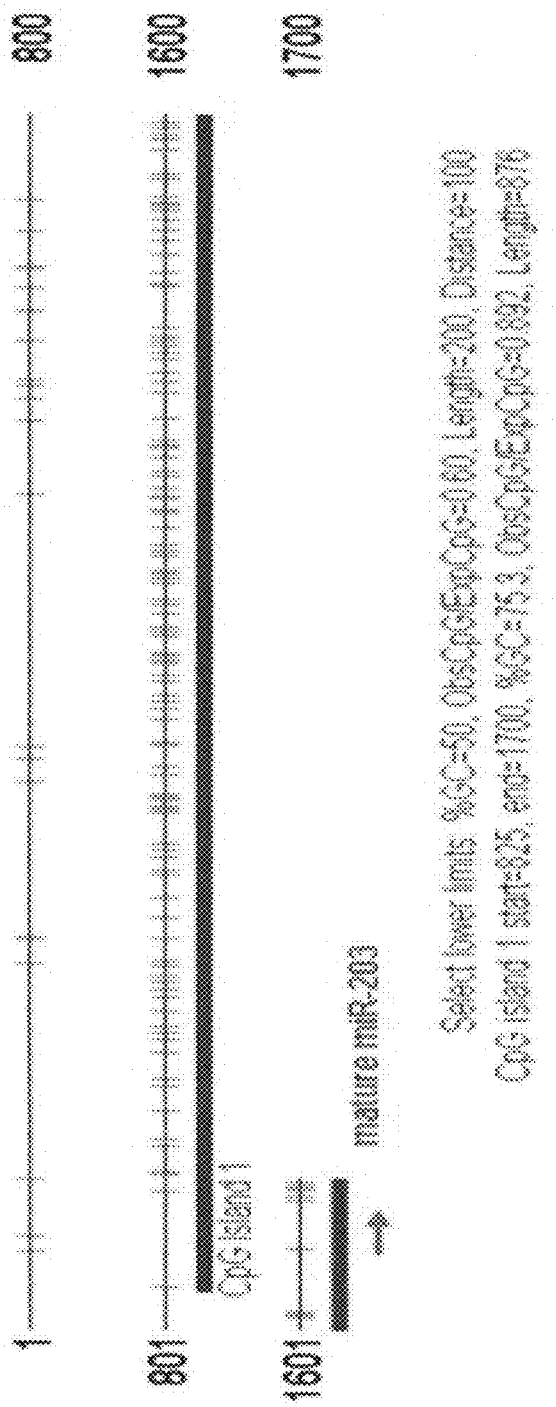

Interestingly, miR-21, miR-203 and miR-205 are overexpressed in ovarian carcinomas compared to normal tissues (see SAM analysis in FIG. 9—Table 2 and Venn Diagram in FIGS. 3A and 3B): the reactivation of these miR genes after demethylating treatment suggests that the hypomethylation could be the mechanism responsible for their overexpression in vivo. We confirmed the overexpression of miR-21, the most significant miR induced upon treatment, performing a Northern Blotting (FIG. 7A) on a panel of human ovarian carcinomas and two normal tissues. Moreover, using the CpG Island Searcher Program (34), we verified that miR-21 and miR-203 are associated with CpG islands, being the miR-203 embedded in a CpG island 875 bp long, and the miR-21 characterized by a CpG island −2 kb upstream the mature sequence (FIG. 7B), while miR-205 does not show any CpG island in a region spanning 2 Kb upstream its mature form.

Discussion

In the Examples herein, it is now shown that microRNAs are aberrantly expressed in human ovarian cancer. The overall microRNA expression can clearly separate normal versus cancer tissues, identifying a number of microRNAs altered in human ovarian cancer and probably involved in the development of this neoplasia.

1. The expression of all the four microRNAs we found most significantly up-modulated, miR-200a and miR-141, belonging to the same family; miR-200b (localized in the same region of miR-200a, at chr.1p36.33); and miR-200c, (localized in the same region of miR-141, at chr.12p13.31), is concordant with the results obtained at genomic level by Zhang et al. (MicroRNAs exhibit high frequency genomic alterations in human cancer. Proc Natl Acad Sci USA. 2006; 103:9136-41), suggesting that the mechanism driving their up-modulation could be the amplification of the microRNA genes.

Interestingly, all these miRs have a common putative target: the oncosuppressor BAP1, BRCA1-associated protein. The altered expression of GATA factors, found and proposed as the underlying mechanism for dedifferentiation in ovarian carcinogenesis, may also be driven by microRNAs deregulation. In particular GATA6, lost or excluded from the nucleus in 85% of ovarian tumors, may be regulated by miR-200a, and GATA4, absent in the majority of ovarian cancer cell lines, may be targeted by miR-200b (FIG. 12—Table 5).

Among the down-modulated genes, notably we found miR-125b1, altered also in breast cancer, as well as miR-145; mir-199a, recently shown down-modulated in other tumors, as hepatocellular carcinoma; miR-140, deleted in ovarian carcinoma.

Interestingly, miR-140 is indeed located at chr.6q22, a fragile region often deleted in ovarian tumor, and it is predicted to target important molecules as c-SRK, MMP13 and FGF2.

Even if the normal control available in these examples is represented by whole normal ovary, our data can identify a number of microRNAs altered in human ovarian carcinoma and probably involved in the biology of this malignancy. In fact, the miRNA signatures obtained comparing different histotypes of ovarian carcinomas (serous, endometrioid, clear cell and mixed) to the normal tissue are overlapping in most cases, but they also reveal a number of microRNAs that seem to be "histotype-specific": the endometrioid tumors, for example, share with the others the 4 most significantly up-modulated miRs (miR-200a, miR200b, miR-200c and miR-141), but also present overexpression of miR-21, known to be mis-regulated in numerous solid tumors and to exert an anti-apoptotic role in different cellular systems, miR-205 and miR-182.

Endometrioid tumors also present down-modulation of several microRNAs in comparison with the other classes of tumors, for example miR-222, already demonstrated targeting c-Kit, being involved in cancer and down-modulated under folate-deficient conditions.

These differences enforce the fact that different histotypes represent biologically and pathogenetically distinct entities of EOCs, even though they are currently treated with identical therapeutic strategies. Microarray analysis has recently confirmed that different histotypes (serous, mucinous, endometrioid and clear cell) show the alteration of different pathways, probably reflecting the gene expression pattern of the organ of origin (respectively fallopian tubes, colonic mucosa and endometrium).

Notably, many of the microRNAs differentially expressed are predicted to target molecules involved in pathways differentially activated depending on the histotype. miR-212, for example, down-modulated in serous carcinoma, has as putative target WT1, overexpressed in this subgroup of ovarian carcinomas. Another putative target of miR-212 is BRCA1: mutated in hereditary ovarian cancer, this molecule has been recently found involved also in the pathoetiology of sporadic ovarian epithelial cancer (OEC), where a loss of gene function due to epigenetic alterations has been observed more commonly. The decreased BRCA1 expression could be determined by overexpression of one or more microRNAs.

miR-299-5p and miR-135b, up-modulated in serous histotype compared to endometrioid, are supposed to target, respectively, DLK1 (Delta-like 1) and MSX2 (msh homeobox 2), overexpressed in endometrioid carcinomas. Compared to the other tumors, clear cell carcinomas show expression levels of miR-30-5p and of miR-20a opposite to two putative targets, RBP4 (retinol binding protein 4) and SLC40A1 (solute carrier 40-iron-regulated transporter, member 1), respectively. Compared to the normal tissue, clear cell carcinoma also show lower expression of miR-18a, miR-19a and miR-19b, suggesting a possible down-modulation of the cluster 17-92 (already validated as deleted by Zhang et al.). This cluster, involved in the intricate regulation mediated by E2F1 and c-Myc, seems to have a duplex nature of putative oncogene, as recently suggested in B-cell Lymphoma, or tumor-suppressor: in hepatocellular carcinoma, for example, LOH at the locus coding the miR-17-92 cluster (13q31) has been reported. In Ovarian Carcinoma, at least in clear cell histotype, it could also exert a role of oncosuppressor. The data shown herein now suggest indeed that microRNAs may have a regulatory role in the process of differentiation leading to the development of a specific subtype of EOC.

Interestingly, poorly differentiated carcinomas have a quite different pattern of microRNAs expression, showing up-modulation of several microRNAs in comparison to normal ovary. More intriguingly, one of them, miR-373, has been recently described as putative oncogene in testicular germ cell tumors.

The absence of microRNAs significantly differentially expressed in relation to tumor Stage or Grade might be explained by the fact that our set of samples is mostly represented by advanced stage tumors, as expected considering the late diagnosis of this kind of neoplasia; however, the difference in size among the different groups of samples could have represented a limit for the statistical analysis. Alternatively, microRNAs might be important for the development of human ovarian carcinoma but not for the progression of the disease.

Resulting from our analyses a number of miRs overexpressed but not reported as amplified in Zhang study, as well as down-modulated but not deleted, the involvement of an epigenetic regulatory mechanism could actually exert a role on microRNA expression in human EOC.

Indeed, among the most significant microRNAs induced after demethylating treatment of an ovarian cell line, we found miR-21, miR-203 and miR-205, up-modulated in ovarian cancer. Moreover, miR-203 and miR-21 are associated with a CpG island (miR-203 is embedded in a CpG island, while miR-21 has a CpG island −2 kb upstream its mature sequence), supporting the idea that the demethylation leads to the reactivation of these microRNA genes. Notably, miR-21 has already been described up-modulated in several human tumors and having an anti-apoptotic role in different cellular models. These data now show that the DNA hypomethylation could be an epigenetic mechanism responsible for the in vivo overexpression of potentially oncogenic miRs.

To the best of the inventor's knowledge, this is the first report describing a complete miRs expression profiling in human EOCs, focused on the identification of miRs differentially expressed in carcinomas versus normal ovary, and in different subgroups of tumors. The data now show the important role that microRNAs can exert on the pathogenesis and on the development of different histotypes of ovarian carcinoma, and identify altered DNA methylation as a possible epigenetic mechanism responsible for the aberrant expression of microRNAs not affected by genomic changes.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

The miR Gene Database

The miRNAs of interest are listed in public databases. In certain preferred embodiments, the public database can be a central repository provided by the Sanger Institute http://microma.sanger.ac.uk/sequences/ to which miRNA sequences are submitted for naming and nomenclature assignment, as well as placement of the sequences in a database for archiving and for online retrieval via the world wide web. Generally, the data collected on the sequences of miRNAs by the Sanger Institute include species, source, corresponding genomic sequences and genomic location (chromosomal coordinates), as well as full length transcription products and sequences for the mature fully processed miRNA (miRNA with a 5' terminal phosphate group). Another database can be the GenBank database accessed through the National Center for Biotechnology Information (NCBI) website, maintained by the National Institutes of Health and the National Library of Medicine. These databases are fully incorporated herein by reference.

| ACCESSION NUMBER | ID | SEQUENCE | SEQ ID NO |
|---|---|---|---|
| MIMAT0000682 | hsa-miR-200a | UAACACUGUCUGGUAACGAUGU | 1 |
| MIMAT0000318 | hsa-miR-200b | UAAUACUGCCUGGUAAUGAUGA | 2 |
| MIMAT0000617 | hsa-miR-200c | UAAUACUGCCGGGUAAUGAUGGA | 3 |
| MIMAT0000432 | hsa-miR-141 | UAACACUGUCUGGUAAAGAUGG | 4 |
| MIMAT0000714 | hsa-miR-302b* | ACUUUAACAUGGAAGUGCUUUC | 5 |
| MIMAT0000259 | hsa-mir-182 | UUUGGCAAUGGUAGAACUCACACU | 6 |
| MIMAT0000771 | hsa-miR-325 | CCUAGUAGGUGUCCAGUAAGUGU | 7 |
| MIMAT0000726 | hsa-miR-373 | GAAGUGCUUCGAUUUUGGGGUGU | 8 |

-continued

| ACCESSION NUMBER | ID | SEQUENCE | SEQ ID NO |
|---|---|---|---|
| MIMAT0000264 | hsa-miR-203 | GUGAAAUGUUUAGGACCACUAG | 9 |
| MIMAT0000266 | hsa-miR-205 | UCCUUCAUUCCACCGGAGUCUG | 10 |
| MIMAT0000231 | hsa-miR-199a | CCCAGUGUUCAGACUACCUGUUC | 11 |
| MIMAT0000263 | hsa-miR-199b | CCCAGUGUUUAGACUAUCUGUUC | 12 |
| MIMAT0000435 | hsa-miR-143 | UGAGAUGAAGCACUGUAGCUC | 13 |
| MIMAT0004604 | hsa-miR-127 | CUGAAGCUCAGAGGGCUCUGAU | 14 |
| MIMAT0000431 | hsa-miR-140 | CAGUGGUUUUACCCUAUGGUAG | 15 |
| MIMAT0000441 | hsa-miR-9 | UCUUUGGUUAUCUAGCUGUAUGA | 16 |
| MIMAT0000427 | hsa-miR-133a | UUUGGUCCCCUUCAACCAGCUG | 17 |
| MIMAT0000102 | hsa-miR-105 | UCAAAUGCUCAGACUCCUGUGGU | 18 |
| MIMAT0000099 | hsa-miR-101 | UACAGUACUGUGAUAACUGAA | 19 |
| MIMAT0000281 | hsa-miR-224 | CAAGUCACUAGUGGUUCCGUU | 20 |
| MIMAT0000445 | hsa-miR-126 | UCGUACCGUGAGUAAUAAUGCG | 21 |
| MIMAT0000098 | hsa-miR-100 | AACCCGUAGAUCCGAACUUGUG | 22 |
| MIMAT0000251 | hsa-miR-147 | GUGUGUGGAAAUGCUUCUGC | 23 |
| MIMAT0000265 | hsa-miR-204 | UUCCCUUUGUCAUCCUAUGCCU | 24 |
| MIMAT0000271 | hsa-miR-214 | ACAGCAGGCACAGACAGGCAGU | 25 |
| MIMAT0000097 | hsa-miR-99a | AACCCGUAGAUCCGAUCUUGUG | 26 |
| MIMAT0000268 | hsa-miR-211 | UUCCCUUUGUCAUCCUUCGCCU | 27 |
| MIMAT0000437 | hsa-miR-145 | GUCCAGUUUUCCCAGGAAUCCCU | 28 |
| MIMAT0000065 | hsa-let-7d | AGAGGUAGUAGGUUGCAUAGUU | 29 |
| MIMAT0000422 | hsa-miR-124 | UAAGGCACGCGGUGAAUGCC | 30 |
| MIMAT0000443 | hsa-miR-125a | UCCCUGAGACCCUUUAACCUGUGA | 31 |
| MIMAT0000064 | hsa-let-7c | UGAGGUAGUAGGUUGUAUGGUU | 32 |
| MIMAT0000062 | hsa-let-7a | UGAGGUAGUAGGUUGUAUAGUU | 33 |

-continued

| ACCESSION NUMBER | ID | SEQUENCE | SEQ ID NO |
|---|---|---|---|
| MIMAT0000681 | hsa-miR-29c | UAGCACCAUUUGAAAUCGGUUA | 34 |
| MIMAT0000461 | hsa-miR-195 | UAGCAGCACAGAAAUAUUGGC | 35 |
| MIMAT0000423 | hsa-miR-125b | UCCCUGAGACCCUAACUUGUGA | 36 |
| MIMAT0000727 | hsa-miR-374 | UUAUAAUACAACCUGAUAAGUG | 37 |
| MIMAT0000715 | hsa-miR-302b | UAAGUGCUUCCAUGUUUUAGUAG | 38 |
| MIMAT0000086 | hsa-miR-29a | UAGCACCAUCUGAAAUCGGUUA | 39 |
| MIMAT0000076 | hsa-miR-21 | UAGCUUAUCAGACUGAUGUUGA | 40 |
| MIMAT0000259 | hsa-miR-182 | UUUGGCAAUGGUAGAACUCACACU | 41 |
| MIMAT0000270 | hsa-miR-181a* | ACCAUCGACCGUUGAUUGUACC | 42 |
| MIMAT0000273 | hsa-miR-216 | UAAUCUCAGCUGGCAACUGUGA | 43 |
| MIMAT0000717 | hsa-miR-302c | UAAGUGCUUCCAUGUUUCAGUGG | 44 |
| MIMAT0000688 | hsa-miR-301a | CAGUGCAAUAGUAUUGUCAAAGC | 45 |
| MIMAT0000096 | hsa-miR-98 | UGAGGUAGUAAGUUGUAUUGUU | 46 |
| MIMAT0000074 | hsa-miR-19b | UGUGCAAAUCCAUGCAAAACUGA | 47 |
| MIMAT0000100 | hsa-miR-29b | UAGCACCAUUUGAAAUCAGUGUU | 48 |
| MIMAT0000072 | hsa-miR-18a | UAAGGUGCAUCUAGUGCAGAUAG | 49 |
| MIMAT0000452 | hsa-miR-154 | UAGGUUAUCCGUGUUGCCUUCG | 50 |
| MIMAT0000073 | hsa-miR-19a | UGUGCAAAUCUAUGCAAAACUGA | 51 |
| MIMAT0000439 | hsa-miR-153 | UUGCAUAGUCACAAAAGUGAUC | 52 |
| MIMAT0000436 | hsa-miR-144 | UACAGUAUAGAUGAUGUACU | 53 |
| MIMAT0000279 | hsa-miR-222 | AGCUACAUCUGGCUACUGGGU | 54 |
| MIMAT0000416 | hsa-miR-1 | UGGAAUGUAAAGAAGUAUGUAU | 55 |
| MIMAT0000684 | hsa-miR-302a | UAAGUGCUUCCAUGUUUUGGUGA | 56 |
| MIMAT0000686 | hsa-miR-34c-5p | AGGCAGUGUAGUUAGCUGAUUGC | 57 |
| MIMAT0000272 | hsa-miR-215 | AUGACCUAUGAAUUGACAGAC | 58 |

-continued

| ACCESSION NUMBER | ID | SEQUENCE | SEQ ID NO |
|---|---|---|---|
| MIMAT0000085 | hsa-miR-28-5p | AAGGAGCUCACAGUCUAUUGAG | 59 |
| MIMAT0000770 | hsa-miR-133b | UUUGGUCCCCUUCAACCAGCUA | 60 |
| MIMAT0002890 | hsa-miR-299-5p | UGGUUUACCGUCCCACAUACAU | 61 |
| MIMAT0000252 | hsa-miR-7 | UGGAAGACUAGUGAUUUUGUUGU | 62 |
| MIMAT0000250 | hsa-miR-139-5p | UCUACAGUGCACGUGUCUCCAG | 63 |
| MIMAT0000722 | hsa-miR-370 | GCCUGCUGGGGUGGAACCUGGU | 64 |
| MIMAT0000429 | hsa-miR-137 | UUAUUGCUUAAGAAUACGCGUAG | 65 |
| MIMAT0000442 | hsa-miR-9* | AUAAAGCUAGAUAACCGAAAGU | 66 |
| MIMAT0002809 | hsa-miR-146b-5p | UGAGAACUGAAUUCCAUAGGCU | 67 |
| MIMAT0000087 | hsa-miR-30 | UGUAAACAUCCUCGACUGGAAG | 68 |
| MIMAT0000095 | hsa-miR-96 | UUUGGCACUAGCACAUUUUUGCU | 69 |
| MIMAT0000646 | hsa-miR-155 | UUAAUGCUAAUCGUGAUAGGGGU | 70 |
| MIMAT0000738 | hsa-miR-383 | AGAUCAGAAGGUGAUUGUGGCU | 71 |
| MIMAT0000244 | hsa-miR-30c | UGUAAACAUCCUACACUCUCAGC | 72 |
| MIMAT0002819 | hsa-miR-193b | AACUGGCCCUCAAAGUCCCGCU | 73 |
| MIMAT0002811 | hsa-miR-202 | AGAGGUAUAGGGCAUGGGAA | 74 |
| MIMAT0000447 | hsa-miR-134 | UGUGACUGGUUGACCAGAGGGG | 75 |
| MIMAT0004696 | hsa-miR-323-5p | AGGUGGUCCGUGGCGCGUUCGC | 76 |

-continued

| ACCESSION NUMBER | ID | SEQUENCE | SEQ ID NO |
|---|---|---|---|
| MIMAT0004695 | hsa-miR-337-5p | GAACGGCUUCAUACAGGAGUU | 77 |
| MIMAT0000254 | hsa-miR-10b | UACCCUGUAGAACCGAAUUUGUG | 78 |
| MIMAT0000077 | hsa-miR-22 | AAGCUGCCAGUUGAAGAACUGU | 79 |
| MIMAT0001080 | hsa-miR-196b | UAGGUAGUUUCCUGUUGUUGGG | 80 |
| MIMAT0000460 | hsa-miR-194 | UGUAACAGCAACUCCAUGUGGA | 81 |
| MIMAT0000761 | hsa-miR-324-5p | CGCAUCCCCUAGGGCAUUGGUGU | 82 |
| MIMAT0000758 | hsa-miR-135b | UAUGGCUUUUCAUUCCUAUGUGA | 83 |
| MIMAT0000269 | hsa-miR-212 | UAACAGUCUCCAGUCACGGCC | 84 |
| MIMAT0000451 | hsa-miR-150 | UCUCCCAACCCUUGUACCAGUG | 85 |
| MIMAT0000759 | hsa-miR-148b | UCAGUGCAUCACAGAACUUUGU | 86 |
| MIMAT0000692 | hsa-miR-30e | UGUAAACAUCCUUGACUGGAAG | 87 |
| MIMAT0000075 | hsa-miR-20a | UAAAGUGCUUAUAGUGCAGGUAG | 88 |
| MIMAT0000256 | hsa-miR-181a | AACAUUCAACGCUGUCGGUGAGU | 89 |
| MIMAT0000449 | hsa-miR-146a | UGAGAACUGAAUUCCAUGGGUU | 90 |
| MIMAT0004614 | hsa-miR-193a-5p | UGGGUCUUUGCGGGCGAGAUGA | 91 |

REFERENCES

The references discussed above and the following references, to the extent that they provide exemplary procedural or other details supplementary to those set forth herein, are specifically incorporated herein by reference.

What is claimed is:

1. A method to measure miRNA in a subject, the method consisting of:

receiving a test sample extracted from the subject, the test sample comprising ovarian tissue;

receiving a control sample extracted from the subject, the control sample comprising normal ovarian tissue, and measuring levels of miRNA gene products in the test sample and in the control sample, wherein the measuring levels of miRNA gene products in the test sample and in the control sample consists of measuring levels of miR-200a, miR-200c, miR-204, miR-101-1, miR-214, miR-34c, miR-374, miR-195, miR-215, miR-28, miR-29a, and miR-133b.

* * * * *